(12) United States Patent
Lenhert

(10) Patent No.: US 9,102,974 B2
(45) Date of Patent: Aug. 11, 2015

(54) SEMI-SYNTHETIC QUORUM SENSORS

(75) Inventor: Steven Lenhert, Tallahassee, FL (US)

(73) Assignee: Florida State University Research Foundation, Inc., Tallahassee, FL (US)

(*) Notice: Subject to any disclaimer, the term of this patent is extended or adjusted under 35 U.S.C. 154(b) by 986 days.

(21) Appl. No.: 13/248,250

(22) Filed: Sep. 29, 2011

(65) Prior Publication Data

US 2012/0075441 A1  Mar. 29, 2012

Related U.S. Application Data

(60) Provisional application No. 61/387,556, filed on Sep. 29, 2010.

(51) Int. Cl.
| | | |
|---|---|---|
| *H04N 7/18* | (2006.01) | |
| *C12Q 1/00* | (2006.01) | |
| *G01N 21/47* | (2006.01) | |
| *G01N 21/64* | (2006.01) | |

(52) U.S. Cl.
CPC ............ *C12Q 1/001* (2013.01); *G01N 21/4788* (2013.01); *G01N 21/6428* (2013.01); *G01N 21/6452* (2013.01)

(58) Field of Classification Search
CPC .......... G01N 21/4788; G01N 21/6428; G01N 21/6452; G01N 2405/00; G01N 33/5029; G01N 33/54366; G01N 33/5008; G01N 33/5076; G01N 33/5432; B01J 19/0046; B01J 2219/00599; B01J 2219/00659; C12Q 1/001
See application file for complete search history.

(56) References Cited

U.S. PATENT DOCUMENTS

| | | |
|---|---|---|
| 6,855,513 B1 | 2/2005 | Whiteley et al. |
| 7,427,408 B2 | 9/2008 | Merritt et al. |
| 2009/0012104 A1* | 1/2009 | Babu et al. ................. 514/265.1 |
| 2009/0176265 A1* | 7/2009 | Stencel et al. .................. 435/29 |
| 2009/0215079 A1* | 8/2009 | Ostermann et al. ............ 435/7.2 |

OTHER PUBLICATIONS

Miller et al. Quorum Sensing in Bacteria, 2001, Department of Molecular Biology, Princeton University, Princeton, New Jersy.*
Ginger, D. S., Zhang, H. & Mirkin, C. A. The evolution of dip-pen nanolithography, Angew. Chem. Int. Ed. 43, 30-45 (2004).
Salaita, K., Wang, Y. H. & Mirkin, C. A. Applications of dip-pen nanolithography, Nature Nanotech. 2, 145-155 (2007).
Mathieu M. et al., "Temporarl stability of photothermally fabricated micropatterns in supported phospholip multilayers", J. Vac. Sci. Technol. A, vol. 28, p. 953 (2010).

(Continued)

*Primary Examiner* — Sath V Perungavoor
*Assistant Examiner* — Nathnael Aynalem
(74) *Attorney, Agent, or Firm* — Alchemy-Partners, PC

(57) ABSTRACT

Described is a device comprising a substrate, and a quorum sensor array on the substrate. The quorum sensor array comprises quorum sensors that release signal molecules in response to one or more environmental signals being sense by the quorum sensors to thereby amplify the one or more environmental signals by causing a signal chain reaction in neighboring quorum sensors of the quorum sensor array. Each of the quorum sensors comprises a lipid multilayer structure. Also described is a method comprising providing data for changes in optical properties of at least part of the quorum sensor array in response to exposing the quorum sensor array to one or more environmental signals, and determining the presence of the one or more environmental signals based on the data.

25 Claims, 24 Drawing Sheets

(56) References Cited

OTHER PUBLICATIONS

Mennicke U. et al., "Preparation of Solid-Supported Lipid Bilayers by Spin-Coating", Langmuir, vol. 18, p. 8172 (2002).

Trapp M. et al., "Hydration dependent studies of highly aligned multilayer lipid membranes by neutron scattering", J. Chem. Phys., 133, 164505 (2010).

Eggeling C. et al., "Direct Observation of the nanoscale dynamics of membrane lipids in a living cell", Nature 457, 1159 (Feb. 26, 2009).

Pompeo G. et al., "AFM characterization of solid-supported lipid multilayers prepared by spin-coating", Biomembranes, vol. 1712, p. 29 (Jun. 15, 2005).

Scheres L. et al., "Micro- and Nanopatterning of Functional Organic Monolayers on Oxide-Free Silicon by Laser-Induced Photothermal Desorption", Small, vol. 6, Isuse 17, p. 1918 (Sep. 6, 2010).

Le Berre M. et al., "From Convective Assembly to Landau-Levich Deposition of Multilayered Phospholipid Films of Controlled Thickness", Langmuir, 25, p. 2554 (2009).

Diguet A. et al., "Preparation of Phospholipid Multilayer Patterns of Controlled Size and Thickness by Capillary Assembly on a Microstructured Substrate", Small, vol. 5, Issue 14, p. 1661 (Jul. 17, 2009).

Lenhert S. et al., "Massively Parallel Dip-Pen Nanolithography of Heterogeneous Supported Phospholipid Multilayer Patterns", Small, vol. 3, pp. 71-75 (Jan. 2, 2007).

Lenhert S. et al., "Lipid multilayer gratings", Nat. Nanotechnology 5, pp. 275-279 (2010).

Lenhert S. et al., "Materials Integration by Dip-pen Nanolithography", published Jul. 15, 2010.

Braunschweig A. B. et al., "Molecular printing", Nat. Chem., vol. 1, p. 353 (Aug. 2009).

Zhang H. et al., "High-Throughput Dip-Pen-Nanolithography-Based Fabrication of Si Nanostructures", Small, vol. 3, Issue 1, pp. 81-85, Jan. 2, 2007.

Li B. et al., "Patterning Colloidal Metal Nanoparticles for Controlled Growth of Carbon Nanotubes", Advanced Materials, vol. 20, Issue 24, pp. 4873-4878, Dec. 17, 2008.

Li H. et al., "Nanoscale-Controlled Enzymatic Degradation of Poly(L-lactic acid) Films Using Dip-Pen Nanolithography", Small, vol. 7, Issue 2, pp. 226-229, Jan. 17, 2011.

Haaheim J. et al., "Dip Pen Nanolithography: A 'Desktop Nanofab' Approach Using High-Throughput Flexible Nanopatterning", Scanning, vol. 30, Issue 2, pp. 137-150 (Mar./Apr. 2008).

Sekula S. et al., "Multiplexed Lipid Dip-Pen Nanolithography on Subcellular Scales for the Templating of Functional Proteins and Cell Culture", Small, vol. 4, Issue 10, pp. 1785-1793, Oct. 2008.

Wang Y. H. et al., "A Self-Correcting Inking Strategy for Cantilever Arrays Addressed by an Inkjet Printer and Used for Dip-Pen Nanolithography", Small, vol. 4, Issue 10, pp. 1666-1670, Oct. 2008.

Tamir. T. et al., "Analysis and design of grating couplers", Appl. Phys. 14, 235-254 (1977).

Henzi, P. et al., "Low cost single mode waveguide fabrication allowing passive fiber coupling using LIGA and UV flood exposure", Proc. SPIE 5454, 64-74 (2004).

Sanii, B. et al., "Surface-energy dependent spreading of lipid monolayers and bilayers", Soft Matter 3, 974-977 (2007).

Nissen, J. et al., "Wetting of phospholipid membranes on hydrophilic surfaces—concepts towards self-healing membranes", Eur. Phys. J. B, vol. 10, 335-344 (1999).

Radler, J. et al., Phenomenology and kinetics of lipid bilayer spreading on hydrophilic surfaces, Langmuir, 11, pp. 4539-4548 (1995).

Ulrich, A. S., et al., Hydration of DOPC bilayers by differential scanning calorimetry, BBA Biomembranes 1191, 225-230 (1994).

Rentzhog, M. et al., Print quality and resistance for water-based flexography on polymer-coated boards: dependence on ink formulation and substrate pretreatment, Prog. Org. Coat., vol. 57, Issue 3, pp. 183-194 (2006).

Kumar, A., et al., "Patterned condensation figures as optical diffraction gratings", Science 263, 60-62 (1994).

Chiu, D. T. et al., "Chemical transformations in individual ultrasmall biomimetic containers", Science 283, 1892-95 (1999).

Tanaka M., et al., "Review Article Polymer-supported membranes as models of the cell surface", Nature 437, 656-663 (2005).

Anrather, D. et al., "Supported Membrane Nanodevices", J. Nanosci. Nanotechnol. 4, pp. 1-22 (2004).

Demers, L. M., et al., "Direct Patterning of Modified Oligonucleotides on Metals and Insulators by Dip-Pen Nanolithography", Science, vol. 296, No. 5574, pp. 1836-1838 (Jun. 7, 2002).

Lee, K. B. et al., "Protein Nanostructures Formed via Direct-Write Dip-Pen nanolithography," J. Am. Chem. Soc., 125, pp. 5588-5589 (2003).

Huang, L. et al., "Matrix-assisted dip-pen nanolithography and polymer pen lithography", Small, vol. 6, Issue 10, pp. 1077-1081 (May 21, 2010).

Bellido E. et al., "Controlling the Number of Proteins with Dip-Pen Nanolithography", Advanced Materials, vol. 22, Issue 3, pp. 352-355 (Jan. 19, 2010.

* cited by examiner

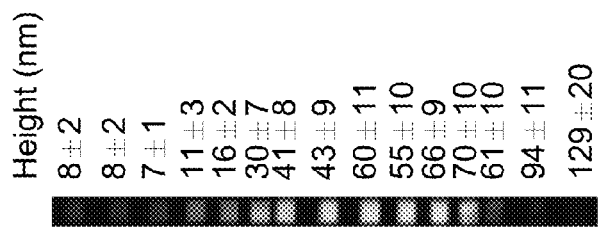
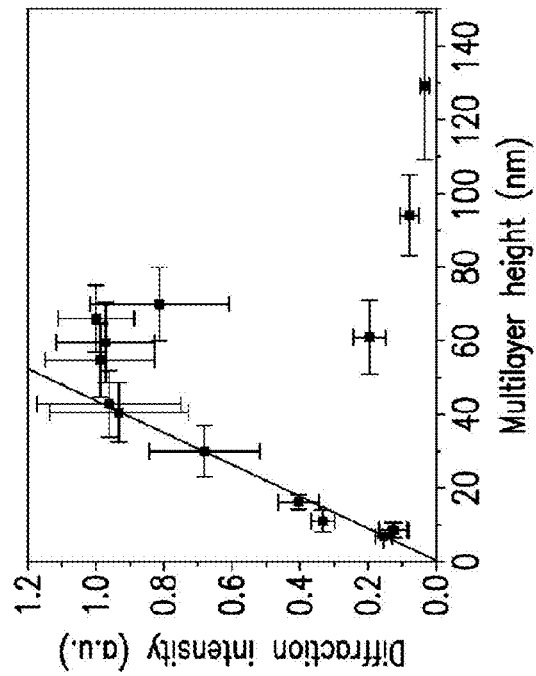
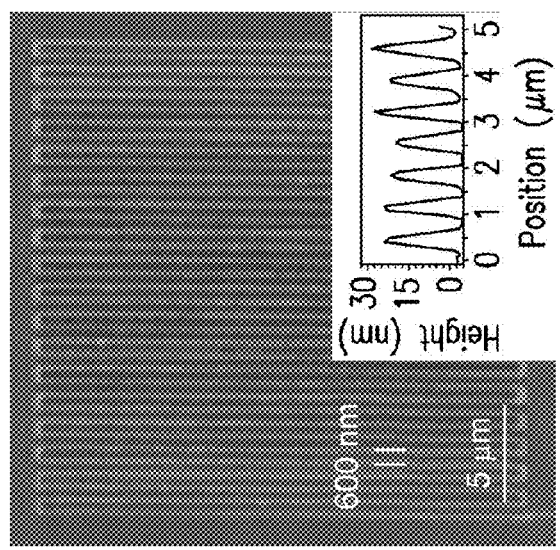
FIG. 4
FIG. 5
FIG. 6

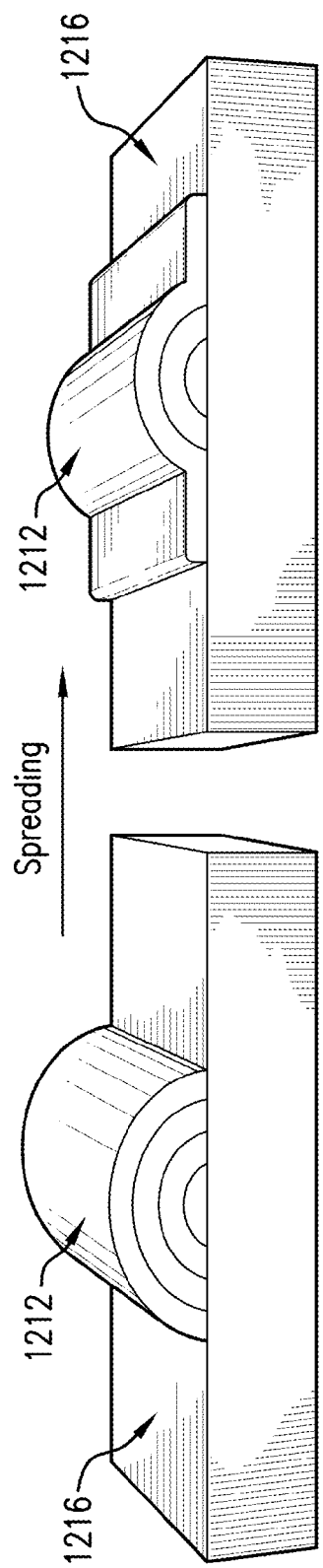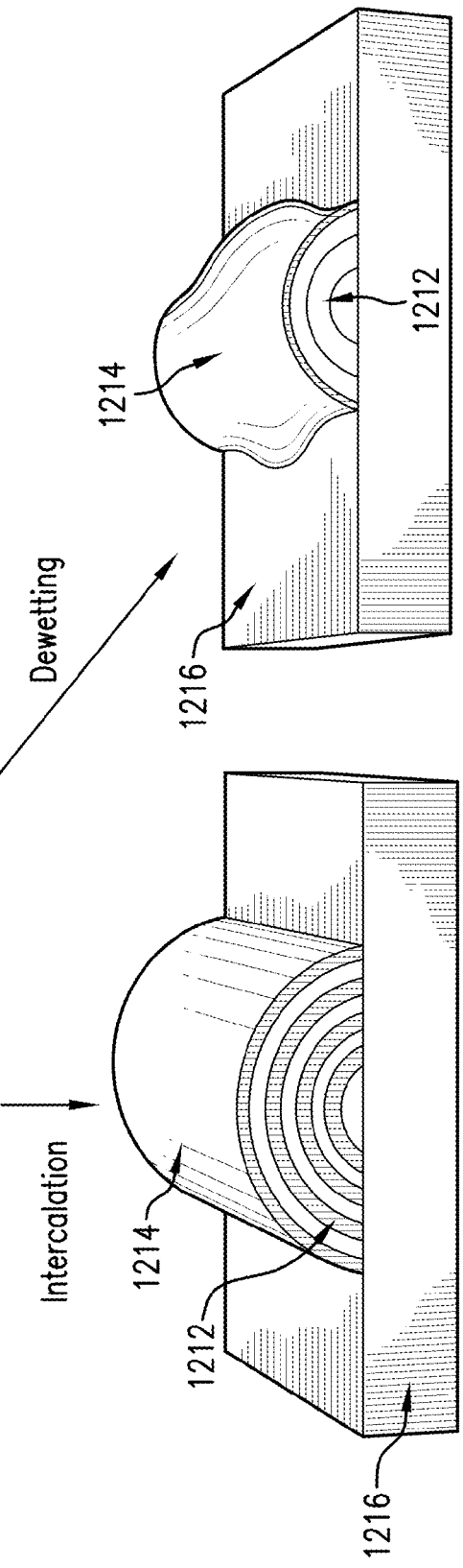

SEMI-SYNTHETIC QUORUM SENSORS

CROSS-REFERENCE TO RELATED APPLICATIONS

This application claims benefit of priority to U.S. Provisional Application No. 61/387,556, to Lenhert, entitled "LIPID MULTILAYER GRATINGS FOR SEMI-SYNTHETIC QUORUM SENSORS," filed Sep. 29, 2010, the entire content and disclosures of which are incorporated herein by reference in their entirety. The present application also makes reference to U.S. patent application Ser. No. 13/234,540, to Lenhert et al. entitled "OPTICAL METHOD FOR MEASURING HEIGHT OF FLUORESCENT PHOSPHOLIPID FEATURES FABRICATED VIA DIP-PEN NANOLITHOGRAPHY" filed Sep. 16, 2011, and U.S. patent application Ser. No. 13/238,498, to Lenhert entitled "INTEGRATED DEVICE FOR ANALYZING AQUEOUS SAMPLES USING LIPID MULTILAYER GRATINGS" filed Sep. 21, 2011, and the entire disclosures and contents of these applications are incorporated herein by reference.

BACKGROUND

1. Field of the Invention

The present invention relates to quorum sensors.

2. Related Art

One difficulty in using bacteria for environmental monitoring is immobilizing the bacteria without affecting the behavior of the bacteria.

SUMMARY

According to a first broad aspect, the present invention provides a device comprising: a substrate, and a quorum sensor array on the substrate, wherein the quorum sensor array comprises quorum sensors that release signal molecules in response to one or more environmental signals being sensed by the quorum sensors to thereby amplify the one or more environmental signals by causing a signal chain reaction in neighboring quorum sensors of the quorum sensor array, and wherein each of the quorum sensors comprises a lipid multilayer structure.

According to a second broad aspect, the present invention provides a method comprising the following steps: (a) providing data for changes in optical properties of at least part of a quorum sensor array in response to exposing the quorum sensor array to one or more environmental signals, and (b) determining the presence of the one or more environmental signals based on the data of step (a), wherein the quorum sensor array comprises quorum sensors that release signal molecules in response to the one or more environmental signals interacting the quorum sensors to thereby amplify the one or more environmental signals by causing a signal chain reaction in neighboring quorum sensors of the quorum sensor array, and wherein each of the quorum sensors comprise a lipid multilayer structure.

According to a third broad aspect, the present invention provides a method comprising the following steps: (a) calibrating a camera based on a calibration profile, (b) detecting with the calibrated camera one or more light intensities of light scattered by one or more iridescent microstructures of a sample, and (c) determining a height of each of one or more iridescent microstructures of the sample based on the one or more light intensities detected in step (b), wherein the calibration profile is based on the one or more light intensities detected by the camera for light scattered by one or more patterned arrays of standard iridescent microstructures of a calibration standard, and wherein each of the patterned arrays of standard iridescent microstructures comprises iridescent microstructures having the same shape and two or more different heights.

According to a fourth broad aspect, the present invention provides a method comprising the following steps: (a) detecting with a camera one or more light intensities of light scattered by one or more iridescent microstructures of a sample, and (b) determining a height of each of the one or more iridescent microstructures of the sample based on one or more light intensities detected in step (a) and a calibration profile for the camera, wherein the calibration profile is based on light intensities detected by the camera for light scattered one or more patterned arrays of standard iridescent microstructures of a calibration standard, and wherein each of the patterned arrays of iridescent microstructures comprises iridescent microstructures having the same shape and two or more different heights.

BRIEF DESCRIPTION OF THE DRAWINGS

The accompanying drawings, which are incorporated herein and constitute part of this specification, illustrate exemplary embodiments of the invention and, together with the general description given above and the detailed description given below, serve to explain the features of the invention.

FIG. 4 is an AFM topographical image of a grating with a period of 600 nm and height of (29+3) nm.

FIG. 5 is a graph showing the correlation between the grating heights (measured by AFM) and the measured intensity of light diffracted from gratings with a period of 600 nm.

FIG. 6 is an optical micrograph of the diffraction from the gratings of FIG. 5 and their measured AFM heights.

FIG. 12 is a schematic diagram of three effects observed as a result of lipid adhesion with a substrate and interaction with protein from solution.

DETAILED DESCRIPTION OF THE PREFERRED EMBODIMENTS

Definitions

Figure 1:
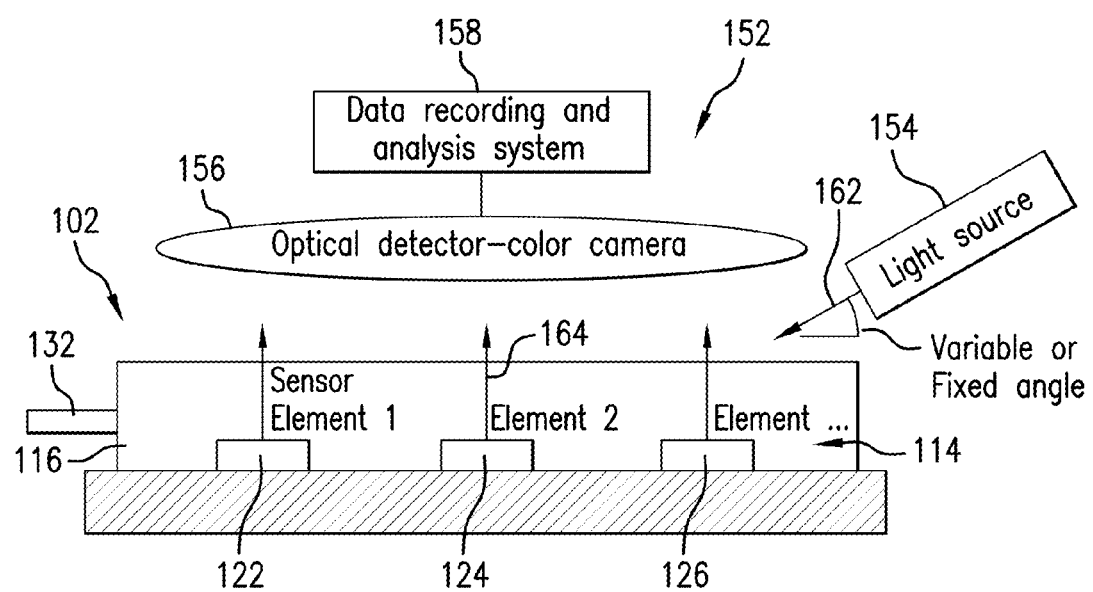
FIG. 1 is a schematic drawing of a lab-on-a-chip sensor device according to one embodiment of the present invention.

Where the definition of a term departs from the commonly used meaning of the term, applicant intends to utilize the definitions provided below, unless specifically indicated.

For purposes of the present invention, it should be noted that the singular forms, "a," "an," and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc. are used merely for convenience in describing the various embodiments of the present invention. The embodiments of the present invention may be oriented in various ways. For example, the diagrams, apparatuses, etc. shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "analyte" refers to the conventional meaning of the term "analyte," i.e., a substance or chemical constituent of a sample that is being detected or measured in a sample. In one embodiment of the present invention, a sample to be analyzed may be an aqueous sample, but other types of samples may also be analyzed using a device of the present invention.

For purposes of the present invention, the term "array" refers to a one-dimensional or two-dimensional set of microstructures. An array may be any shape. For example, an array may be a series of microstructures arranged in a line, such as the array of squares. An array may be arranged in a square or rectangular grid. There may be sections of the array that are separated from other sections of the array by spaces. An array may have other shapes. For example, an array may be a series of microstructures arranged in a series of concentric circles, in a series of concentric squares, a series of concentric triangles, a series of curves, etc. The spacing between sections of an array or between microstructures in any array may be regular or may be different between particular sections or between particular pairs of microstructures. The microstructure arrays of the present invention may be comprised of microstructures having zero-dimensional, one-dimensional or two-dimensional shapes. The microstructures having two-dimensional shapes may have shapes such as squares, rectangles, circles, parallelograms, pentagons, hexagons, irregular shapes, etc. In one embodiment of the present invention, a quorum sensor array, i.e., an array of quorum sensors, is an array of bacteria adhered to a lipid multilayer grating.

For purposes of the present invention, the term "autoinducer" and the term "autoinducer compound" refer to molecules, e.g., proteins which freely diffuse across cell membranes and which activate transcription of various factors which affect bacterial viability. Such compounds can affect virulence, and biofilm development. Autoinducer compounds may be acylated homoserine lactones, but they may also be other types of compounds. Homoserine autoinducer compounds are produced in vivo by the interaction of a homoserine lactone substrate and an acylated acyl carrier protein in a reaction catalyzed by an autoinducer synthase molecule. In isolated form, autoinducer compounds may be obtained from naturally occurring proteins by purifying cellular extracts, or they may be chemically synthesized or recombinantly produced. The language "autoinducer synthase molecule" is intended to include molecules, e.g. proteins, which catalyze or facilitate the synthesis of autoinducer compounds, e.g. in the quorum sensing system of bacteria. Autoinducer compounds include active portions of the autoinducer synthase protein contained in the protein or in fragments or portions of the protein (e.g., a biologically active fragment). The language "active portions" is intended to include the portions of the autoinducer synthase protein which contain the homoserine lactone binding site.

For purposes of the present invention, the term "biomolecule" refers to the conventional meaning of the term biomolecule, i.e., a molecule produced by or found in living cells, e.g., a protein, a carbohydrate, a lipid, a phospholipid, a nucleic acid, etc.

For purposes of the present invention, the term "calibration profile" refers to one or more calibration curves based on light intensity or optical property data for one more respective arrays of microstructure in which the microstructures of each array have the same shape and two or more different heights. In one embodiment of the present invention, a calibration profile may be based on intensity data for one or more respective arrays of fluorescent microstructures in which the fluorescent microstructures of each array have the same shape and two or more different heights. The calibration curves and calibration profile may be adjusted based on the differences between the measured heights of the fluorescent microstructures of the arrays of the calibration standard and the heights determined from the calibration determined solely by the fluorescence intensities detected by a camera, including detection at different exposure conditions, such as exposure time, lamp intensities, light path adjustments, hardware or software gain, etc. for the fluorescent microstructures of the arrays of the calibration standard. In another embodiment of the present invention, the calibration profile may be based on intensity data for one or more respective arrays of iridescent microstructures in which the iridescent microstructures of each array have the same shape and two or more different heights. The calibration curves and calibration profile may be adjusted based on the differences between the measured heights of the iridescent microstructures of the arrays of the calibration standard and the heights determined from the calibration determined solely by the intensities of scattered light detected by a camera, including detection at different exposure conditions, such as exposure time, lamp intensities, light path adjustments, hardware or software gain, etc. for the iridescent microstructures of the arrays of the calibration standard. Within an array of microstructures that is used to obtain a calibration profile, two or more microstructures may have the same height.

For purposes of the present invention, the term "calibration standard" refers to one or more arrays of fluorescent microstructures or iridescent microstructures on a substrate in which one or more of the fluorescent or iridescent microstructures have known or predetermined heights. The heights of the fluorescent or iridescent microstructures of the one or more arrays of a calibration standard may be measured by various means to determine the height of one or more of the fluorescent or iridescent microstructures and this information may be recorded for this calibration standard. A camera may be used to determine the heights of the fluorescent or iridescent microstructures of the one or more arrays of the calibration standard to generate calibration curves and a calibration profile for the calibration standard for that camera or camera type. In one embodiment of the present invention, the calibration curves and calibration profile may be adjusted based on the differences between the measured heights of the fluorescent microstructures of the arrays of the calibration standard and the heights determined from the calibration determined by the fluorescence intensities detected by the camera for the fluorescent microstructures of the arrays of the calibration standard. In another embodiment of the present invention, the calibration curves and calibration profile may be adjusted based on the differences between the measured heights of the iridescent microstructures of the arrays of the calibration standard and the heights determined from the calibration determined by the intensities of light scattered by the iridescent structures and detected by the camera for the iridescent microstructures of the arrays of the calibration standard.

For purposes of the present invention, the term "camera" refers to any type of camera or other device that senses light intensity. Examples of cameras include digital cameras, scanners, charged-coupled devices, CMOS sensors, photomultiplier tubes, analog cameras such as film cameras, etc. A camera may include additional lenses and filters such as the lenses of a microscope apparatus that may adjusted when the camera is calibrated.

For purposes of the present invention, the term "dehydrated lipid multilayer grating" refers to a lipid multilayer grating that is sufficiently low in water content that it is no longer in fluid phase.

For purposes of the present invention, the term "detector" refers to any type of device that detects or measures light. A camera is a type of detector.

For purposes of the present invention, the term "dot" refers to a microstructure that has a zero-dimensional shape.

For purposes of the present invention, the term "encapsulated" refers to a chemical, a molecule, an organism such as a bacterium, etc. that is fully or partially encapsulated or fully or partially enclosed within a structure such as a lipid multilayer structure.

For purposes of the present invention, the term "environmental signal" refers to any substance, phase change, organism or environmental condition, etc. that may be sensed by a quorum sensor. An example of a substance that may be sensed by a quorum sensor is an analyte which may be liquid, solid, ionic, gaseous, etc. The environmental signal may be the presence of a reaction product or degradation product such reaction product or degradation product of an environmental contaminant. The environmental signal may be a substance in a bodily fluid such as blood, urine, saliva, etc. The environmental signal may be an environmental condition such as temperature, humidity, light, turbidity, acidity, ionic strength, etc.

For purposes of the present invention, the term "fluorescence" refers to the conventional meaning of the term fluorescence, i.e., the emission of light by a substance that has absorbed light or other electromagnetic radiation of a different wavelength.

For purposes of the present invention, the term "fluorescent" refers to any material or mixture of materials that exhibits fluorescence.

For purposes of the present invention, the term "fluorescent dye" refers to any substance or additive that is fluorescent or imparts fluorescence to another material. A fluorescent dye may be organic, inorganic, etc.

For purposes of the present invention, the term "fluorescent microstructure" refers to a microstructure that is fluorescent. A fluorescent microstructure may be made of a naturally fluorescent material or may be made of a nonfluorescent material, such as a phospholipid, doped with a fluorescent dye.

For purposes of the present invention, the term "fluorescent nanostructure" refers to a nanostructure that is fluorescent. A fluorescent nanostructure may be made of a naturally fluorescent material or may be made of a nonfluorescent material, such as a phospholipid, doped with a fluorescent dye.

For purposes of the present invention, the term "fluid" refers to a liquid or a gas.

For purposes of the present invention, the term "freezing by dehydration" refers to removal of residual water content, for instance by incubation in an atmosphere with low water content, for instance a vacuum (<50 mbar) or at relative humidity below 40% (at standard temperature and pressure).

For purposes of the present invention, the term "grating" refers to an array of dots, lines, or a 2D shape that are regularly spaced at a distance that causes coherent scattering of incident light.

For purposes of the present invention, the term "hardware and/or software" refers to functions that may be performed by digital software or digital hardware, or a combination of both digital hardware and digital software.

For purposes of the present invention, the term "height" refers to the maximum thickness of the microstructure on a substrate, i.e., the maximum distance the microstructure projects above the substrate on which it is located.

For purposes of the present invention, the term "inlet" refers to an apparatus for allowing the addition of a fluid, such as a liquid sample, at a controlled speed and direction to a reaction chamber or onto the sensors of a sensor device of the present invention.

For purposes of the present invention, the term "iridescent" refers to any structure that scatters light.

For purposes of the present invention, the term "iridescent microstructure" refers to a microstructure that is iridescent.

For purposes of the present invention, the term "iridescent nanostructure" refers to a nanostructure that is iridescent.

For purposes of the present invention, the term "lab-on-a-chip" refers to a device that integrates one or several laboratory functions on a single chip ranging from only millimeters to a few square centimeters in size. A lab-on-a-chip may be used in combination with a larger chip reader, e.g., including a camera.

For purposes of the present invention, the term "light," unless specified otherwise, refers to any type of electromagnetic radiation. Although in the embodiments described below, the light that is incident on the gratings or sensors is visible light, the light that is incident on the gratings or sensor of the present invention may be any type of electromagnetic radiation including infrared light, ultraviolet light, etc. that may be scattered by a grating or sensor. Although in the embodiments described below, the light that is scattered from the gratings or sensors and detected by a detector is visible light, the light that is scattered by a grating or sensor of the present invention and detected by a detector of the present invention may be any type of electromagnetic radiation including infrared light, ultraviolet light, etc. that may be scattered by a grating or sensor.

For purposes of the present invention, the term "light source" refers to a source of incident light that is scattered by a grating or sensor of the present invention. In one embodiment of the present invention, a light source may be part of a device of the present invention. In one embodiment a light source may be light present in the environment of a sensor or grating of the present invention. For example, in one embodiment of the present invention a light source may be part of a device that is separate from the device that includes the sensors and detector of the present invention. A light source may even be the ambient light of a room in which a grating or sensor of the present invention is located. Examples of a light source include a laser, a light emitting diode (LED), an incandescent light bulb, a compact fluorescent light bulb, a fluorescent light bulb, etc.

For purposes of the present invention, the term "line" refers to a "line" as this term is commonly used in the field of nanolithography to refer to a one-dimensional shape.

For purposes of the present invention, the term "lipid multilayer" refers to a lipid coating that is thicker than one molecule.

For purposes of the present invention, the term "lipid multilayer grating" refers to a grating comprised of lipid multilayers.

For purposes of the present invention, the term "low humidity atmosphere" refers to an atmosphere having a relative humidity of less than 40%.

For purposes of the present invention, the term "lyotropic" refers to the conventional meaning of the term "lyotropic," i.e., a material that forms liquid crystal phases because of the addition of a solvent.

For purposes of the present invention, the term "microstructure" refers to a structure having at least one dimension smaller than 1 mm. A nanostructure is one type of microstructure.

For purposes of the present invention, the term "nanostructure" refers to a structure having at least one dimension on the nanoscale, i.e., a dimension between 0.1 and 100 nm.

For purposes of the present invention, the term "plurality" refers to two or more. So an array of microstructures having a "plurality of heights" is an array of microstructures having two or more heights. However, some of the microstructures in an array having a plurality of heights may have the same height.

For purposes of the present invention, the term "quorum sensing" refers to the conventional meaning of quorum sensing, i.e., a system of stimulus and response correlated to population density. Bacteria, for example, use quorum sensing to coordinate various behaviors based on the local density of the bacterial population. Quorum sensing may occur within a single bacterial species as well as between diverse species. Quorum sensing may be used to regulate various different processes and may be used as a communication network. Various molecules may be used as signals including: oligopeptides, N-acyl homoserine lactones (AHL), autoinducers such as autoinducer-2, etc. In gram-negative bacterial quorum sensing bacteria, intraspecies quorum sensing, i.e., quorum sensing within the same species of bacteria, may involve two proteins, an autoinducer synthase, i.e., the I protein, and the transcriptional activator, i.e., the R protein. The synthase produces an acylated homoserine lactone (the "autoinducer"), which can diffuse into the surrounding environment. The autoinducer molecule is composed of an acyl chain in a peptide bond with the amino nitrogen of a homoserine lactone (HSL). For different quorum sensing systems, the side-chain may vary in length, degree of saturation, and oxidation state. As the density of bacteria increases, so does the concentration of this freely diffusible signal molecule. Once the concentration reaches a defined threshold, it binds to the R-protein, which then activates transcription of numerous genes. Quorum sensing in gram-negative bacteria is described, for example, in U.S. Pat. No. 6,855,513 to Whitely et al., entitled "QUORUM SENSING SIGNALING IN BACTERIA," issued Feb. 15, 2005. Gram-positive bacteria may use various peptides as their chemical signal for intraspecies quorum sensing, as described in U.S. Pat. No. 7,427,408 to Merritt et al., entitled "QUORUM SENSING AND BIOFILM FORMATION," issued Sep. 23, 2008. Merritt et al. also describes interspecies quorum sensing involving the LuxS gene. The entire disclosure and contents of the above-cited patents are incorporated herein by reference.

For purposes of the present invention, the term "quorum sensing communication network" refers to a communication network comprising two or more quorum sensors.

For purposes of the present invention, the term "quorum signal molecule" and the term "signal molecule" refer to a molecule that may be used as a signal in quorum sensing. Examples of quorum sensing molecules include oligopeptides, N-acyl homoserine lactones (AHL), autoinducers such as autoinducer-2, etc. Other molecules that are not used in quorum sensing by bacteria in nature may also be employed as quorum sensing molecules in the quorum sensory arrays of some embodiments of the present invention.

For purposes of the present invention, the term "quorum sensor" refers to a lipid multilayer structure or the combination of one or more cells and a lipid multilayer structure that produces and/or releases one or more signal molecules in response to an environmental signal interacting with the quorum sensor. When the quorum sensor is a lipid multilayer structure of a lipid multilayer grating, the lipid multilayer structure functions as a type of synthetic cell that behave similarly to natural cells such as bacteria. In one embodiment, the one or more cells that are part of the quorum sensor may be a bacteria that are bound to or encapsulated within a lipid multilayer structure. For example, one or more bacteria may be bound to or encapsulated with a dot, a square, a line, etc. of a lipid multilayer grating.

For purposes of the present invention, the term "quorum sensor array" refers to an array of quorum sensors. In one embodiment of the present a quorum sensor array may behave as a type of artificial tissue.

For purposes of the present invention, the term "reaction chamber" refers a chamber in which one or more sensors of a sensor device are exposed to a fluid present in the chamber. In some embodiments of the present invention, a reaction chamber may be an open or closed fluid channel through which a sample or other fluids flow. In some embodiments, a reaction chamber may be a chamber into which a sample may be added to expose the one or more sensors to the sample.

For purposes of the present invention, the term "reactive agent" refers to a material or organism bound to, encapsulated within, complexed with, inserted in, etc. a lipid multilayer grating that will interact with an analyte of a sample and thereby cause the optical properties of the lipid multilayer grating to change. Examples include functional groups, embedded molecules, embedded ions, membrane-bound proteins, living cells, bacteria, nanoparticles, catalysts, etc.

For purposes of the present invention, the term "release mechanism" refers a portion of a quorum sensor that produces and/or releases one or more signal molecules in response a quorum sensor sensing an environmental signal or a signal molecule. The release mechanism may be part of a lipid multilayer structure or part of a cell, such as a bacterium, bound or encapsulated within a lipid multilayer structure. In one embodiment of the present invention, an environmental signal may induce a shape change in the lipid multilayer, for instance by changing an interfacial energy of a fluid lipid multilayer, which results in the release of encapsulated materials. In some embodiments of the present invention, a sensor mechanism may be separate from the release mechanism of quorum senor. For example, in quorum sensors having encapsulated or bound bacteria, the bacteria may have a receptor for a environmental signal condition, i.e., a sensor mechanism, that may be coupled to the production of an autoinducer that is released, i.e., a release mechanism, and causes a signal chain reaction neighboring quorum sensors by causing the bacteria of the neighboring quorum sensors to produce and release the autoinducer. Another example of where the release mechanism and sensor mechanism may be viewed as separate is a lipid multilayer structure that includes a channel in the lipid that only opens when an analyte binds to part of the lipid multilayer structure. In some embodiments of the present sensor mechanism may be part of a release mechanism. For example, one or more microcapsules in the lipid multilayer structure that contain the signal molecules and that dissolve or rupture when exposed to the environmental signal to release the signal molecules, a catalyst that catalyzes a reaction with an analyte to form a sensor molecule, a substance that reacts with an analyte to produce the sensor molecule, one or more microcapsules in the lipid multilayer structure that contain the signal molecules and that dissolve or rupture when exposed to the environmental signal to release the signal molecules, a change in pH causes a change in the conformation of a lipid multilayer structure that causes the release of a signal molecule, an analyte binding to a lipid multilayer structure to cause a change in the shape of the lipid multilayer structure to release a signal molecule, etc. are examples of mechanisms that are both a sensor mechanism and a release mechanism.

For purposes of the present invention, the term "scattering" and the term "light scattering" refer to the scattering of light by deflection of one or more light rays from a straight path due to the interaction of light with a grating or sensor. One type of interaction of light with a grating or sensor that results in scattering is diffraction.

For purposes of the present invention, the term "sensor" and the term "sensor element" are used interchangeably, unless specified otherwise, and refer to a material that may be used to sense the presence of an analyte.

For purposes of the present invention, the term "sensor mechanism" refers to any portion of a quorum sensor that allows the quorum sensor to sense an environmental signal or a signal molecule. The sensing mechanism may be part of a lipid multilayer structure or part of a cell, such as a bacterium, bound or encapsulated within a lipid multilayer structure. In one embodiment of the present invention, an environmental signal may induce a shape change in the lipid multilayer, for instance by changing an interfacial energy of a fluid lipid multilayer, which results in the release of encapsulated materials. In some embodiments of the present invention, a sensor mechanism may be separate from the release mechanism of quorum senor. For example, in quorum sensors having encapsulated or bound bacteria, the bacteria may have a receptor for a environmental signal condition, i.e., a sensor mechanism, that may be coupled to the production of an autoinducer that is released, i.e., a release mechanism, and causes a signal chain reaction neighboring quorum sensors by causing the bacteria of the neighboring quorum sensors to produce and release the autoinducer. Another example of where the release mechanism and sensor mechanism may be viewed as separate is a lipid multilayer structure that includes a channel in the lipid that only opens when an analyte binds to part of the lipid multilayer structure. In some embodiments of the present invention, a sensor mechanism may be part of a release mechanism. For example, one or more microcapsules in the lipid multilayer structure that contain the signal molecules and that dissolve or rupture when exposed to the environmental signal to release the signal molecules, a catalyst that catalyzes a reaction with an analyte to form a sensor molecule, a substance that reacts with an analyte to produce the sensor molecule, one or more microcapsules in the lipid multilayer structure that contain the signal molecules and that dissolve or rupture when exposed to the environmental signal to release the signal molecules, a change in pH causes a change in the conformation of a lipid multilayer structure that causes the release of a signal molecule, an analyte binding to a lipid multilayer structure to cause a change in the shape of the lipid multilayer structure to release a signal molecule, etc. are examples of mechanisms that are both a sensor mechanism and a release mechanism.

For purposes of the present invention, the term "signal chain reaction" refers to the chain reaction in neighboring quorum sensors caused by one or more quorum sensors releasing one or more signal molecules that are sensed by the neighboring quorum sensors and thereby in turn causing the neighboring quorum sensors to release sensing molecules.

For purposes of the present invention, the term "square" refers to a microstructure that is square in shape, i.e., has a two-dimensional shape wherein all sides are equal. Although in the experiments discussed below in the Example 2 the two-dimensional shapes are squares, embodiment of the present invention may also employ other two-dimensional shapes such as rectangles, circles, parallelograms, pentagons, hexagons, etc.

Description

The interaction of biological cells with the complex and dynamic extracellular environment is a fundamental process that allows the hierarchical organization of life on earth. Direct communication between cells, as well as cellular detection of and influence on non-biological cues is mediated by a variety of chemical and physical signals. For example, in the case of bacterial quorum sensing, recent evidence has demonstrated that, in addition to the concentration of signaling molecules, the local (subcellular) dimensions and confined diffusional properties of the environment influence cellular behavior and the resulting induction of genetic reprogramming. An understanding of, and the ability to control these effects by means of nanostructured environments may enable surfaces to be engineered that may both detect and influence processes such as biofouling, host-pathogen interactions and bioremediation.

The interaction of electromagnetic waves with matter can be controlled by structuring the matter on the scale of the wavelength of light, and various photonic components have been made by structuring materials using top-down or bottom-up approaches. Dip-pen nanolithography is a scanning-probe-based fabrication technique that may be used to deposit materials on surfaces with high resolution and, when carried out in parallel, with high throughput.

In one embodiment, the present invention provides lyotropic optical diffraction gratings composed of biofunctional lipid multilayers with controllable heights between ~5 and 100 nm that may be fabricated by lipid dip-pen nanolithography. Multiple materials may be simultaneously written into arbitrary patterns on pre-structured surfaces to generate complex structures and devices, allowing nanostructures to be interfaced by combinations of top-down and bottom-up fabrication methods.

In one embodiment, the present invention provides fluid and biocompatible lipid multilayer gratings that allow label-free and specific detection of lipid-protein interactions in solution. This biosensing capability takes advantage of the adhesion properties of the phospholipid superstructures and the changes in the size and shape of the grating elements that take place in response to analyte binding.

Fundamental photonic components can be generated from a large variety of materials by top-down lithography or bottom-up self-assembly. Examples include simple Bragg gratings, stacks and two- or three-dimensional photonic materials. A major challenge lies in the integration of multiple chemical functionalities for the generation of more complex devices, including the readout system, in a simple and efficient way. Top-down microfabrication strives to fabricate smaller structures from a single material, whereas the bottom-up approach seeks to assemble and integrate small components into larger and more complex devices. Dip-pen nanolithography (DPN) is a unique method of microfabrication and nanofabrication, as it is a direct-write method that allows the bottom-up integration of a variety of materials (especially organic and biological molecules) with both high resolution and high throughput, see Ginger, D. S., Zhang, H. & Mirkin, C. A. The evolution of dip-pen nanolithography, *Angew. Chem. Int. Ed.* 43, 30-45 (2004) and Salaita, K., Wang, Y. H. & Mirkin, C. A. Applications of dip-pen nanolithography, *Nature Nanotech.* 2, 145-155 (2007), the entire contents and disclosures of which are incorporated herein by reference.

Phospholipids are fundamental structural and functional components of biological membranes that are both fluid and responsive to external stimuli. Phospholipids in biological systems form the bilayer structure of cellular membranes, as well as a variety of multilayer structures. Examples of lipid multilayers in biological systems include multilamellar cristae in the mitochondria, thylakoid grana and the cisternae of the Golgi apparatus and endoplasmic reticulum. Synthetic phospholipid multilayers can be fabricated by spin-coating, see Mathieu M., Schunk D., Franzka S., Mayer C. and Hartmann N. 2010 *J. Vac. Sci. Technol.* A 28 953; Mennicke U. and Salditt T. 2002 *Langmuir* 18 8172; controlling hydration between glass slides, see Trapp M., Gutberlet T., Juranyi F., Unruh T., Deme B., Tehei M. and Peters J. 2010 J. Chem. Phys. 133 164505 Eggeling C. et al 2009Nature 457 1159; Langmuir-Blodgett deposition, see Pompeo G., Girasole M., Cricenti A., Cattaruzza F., Flamini A., Prosperi T., Generosi J. and Castellano A. C. 2005 Biomembranes 1712 29; laser writing, see Scheres L., Klingebiel B., ter Maat J., Giesbers M., de Jong H., Hartmann N. and Zuilhof H. 2010 Small 6 1918; dewetting, see Le Berre M., Chen Y. and Baigl D. 2009 Langmuir 25 2554; Diguet A., Le Berre M., Chen Y. and Baigl D. 200Small 5 1661; and dip-pen nanolithography (DPN), see Lenhert S., Sun P., Wang Y. H., Fuchs H. and Mirkin C. A. 2007 Small 3 71, and the entire contents and disclosures of the above articles are incorporated herein by reference.

In the presence of water, phospholipids spontaneously self-organize to form liposomes (or vesicles), which are widely used for a variety of biological and nanotechnological applications. For example, the physical chemistry of liposome adhesion on surfaces is well studied as a model system for cell-surface interactions and surface biofunctionalization in general. Furthermore, liposomes have been used as nanoscale containers with attoliter to zeptoliter volumes and networks for nanoscale transport of materials between vessels. The loading of vesicles (for example, by surface binding, encapsulation or intercalation) with a variety of biofunctional materials such as drugs, nucleic acids and proteins is developed for applications in delivery to biological cells. The structuring of adherent phospholipid multilayers into arbitrary photonic structures according to one embodiment of the present invention therefore provides a new approach for the fabrication and observation of biomimetic nanosystems.

DPN has emerged as a reliable method for creating microstructures with a wide variety of materials on desired surfaces, see Lenhert S. et al 2010 Nat. Nanotechnol. 5 275; Braunschweig A. B., Huo F. W. and Mirkin C. A. 2009 Nat. Chem.1 353; Lenhert S., Fuchs H. and Mirkin C. A. 2009 Materials Integration by Dip-pen Nanolithography (Weinheim: Wiley-VCH); Zhang H., Amro N., Disawal S., Elghanian R., Shile R. and Fragala J. 2007 Small 3 81; Li B., Goh C. F., Zhou X. Z., Lu G., Tantang H., Chen Y. H., Xue C., Boey F. Y. C. and Zhang H. 2008 Adv. Mater. 20 4873; Li H., He Q. Y., Wang X. H., Lu G., Liusman C., Li B., Boey F., Venkatraman S. S. and Zhang H. 2011Small 7 226; Salaita K., Wang Y. H. and Mirkin C. A. 2007 Nat. Nanotechnol. 2 145; Haaheim J. and Nafday O. N. 2008 Scanning 30 137; and Ginger D. S., Zhang H. and Mirkin C. A. 2004 Angew. Chem. Int. Ed. 43 30, the entire contents and disclosures of which are incorporated herein by reference. Using phospholipids as the ink for DPN allows control of the lipid multilayer stacking (height) and biocompatible material integration on solid surfaces, see Sekula S. et al 2008 Small 4 1785; and Wang Y. H., Giam L. R., Park M., Lenhert S., Fuchs H. and Mirkin C. A. 2008 Small 4 1666, the entire contents and disclosures of which are incorporated herein by reference.

The resulting biomimetic lipid structures may be used in cell-surface models, biochemical sensors, drug screening and delivery vehicles, for analysis of cell-cell interactions, and to elucidate the mechanisms of membrane trafficking. Lipid multilayer structures have been fabricated using both serial and massively parallel DPN modes, allowing throughputs on the scale of $cm^2$ $min^{-1}$. The height of phospholipid structures can be tuned by the tip contact time and controlling the relative humidity of the patterning environment in DPN, see Lenhert S., Sun P., Wang Y. H., Fuchs H. and Mirkin C. A. 2007Small 3 71, the entire contents and disclosure of which are incorporated herein by reference.

FIG. 1 illustrates a lab-on-a-chip sensor device 102 according to one embodiment of the present invention that may be fabricated using DPN techniques. Sensor device 102 comprises a substrate 112, a sensor array 114 of sensor elements on substrate 112 and a Reaction chamber 116. Although for simplicity of illustration only three sensor elements of sensor array 114 are shown in FIG., 1, i.e., sensor element 122, sensor element 124 and sensor element 126, but sensor array 114 may include additional sensor elements. Each of the sensor elements comprises a lipid multilayer grating. Reaction chamber 116 may be supplied with fluid by a fluid inlet 132. Also shown in FIG. 1 is a detection apparatus 152 comprising a light source 154 and a camera 156. Camera 156 is connected to a data recording and analysis system 158. When illuminated by light source 154 as shown by arrow 162, the sensor elements of sensory array 114 emit light, as shown by arrows 164, due to fluorescence.

In one embodiment of the present invention, samples containing one or more analytes may be analyzed in the following manner. Light source 154 is used to illuminate the sensor elements of sensor array 114 so that camera 156 can detect how light is scattered by each of the sensor elements of sensor array 114. Reaction chamber 116 is then supplied with a liquid sample containing analytes through fluid inlet 132. After analytes in the sample are allowed to bind, react, form a complex, etc. with the sensor elements of sensory array 114, light source 154 is used to illuminate the sensor elements and camera 156 is used to detect the light scattered by sensor elements of sensor array 114 after the possible interaction of one or more of the analytes with one or more of the sensor elements. Data recording and analysis system 158 is then used to determine if there has been a change in the optical properties in one or more of the sensor elements of sensor array 114.

The light source used to illuminate the sensor array of FIG. 1 may be provided at a variable or at a fixed angle.

The data recording and analysis system may be part of the camera or may be a separate computer, laptop computer, tablet computer, smartphone, electronic device, electronic instrument, etc. that is in wired or wireless communication with the camera.

Although not shown in FIG. 1, a reaction chamber of the present invention may include an outlet to allow fluid, such as a sample, to flow through the reaction chamber.

Figure 2:
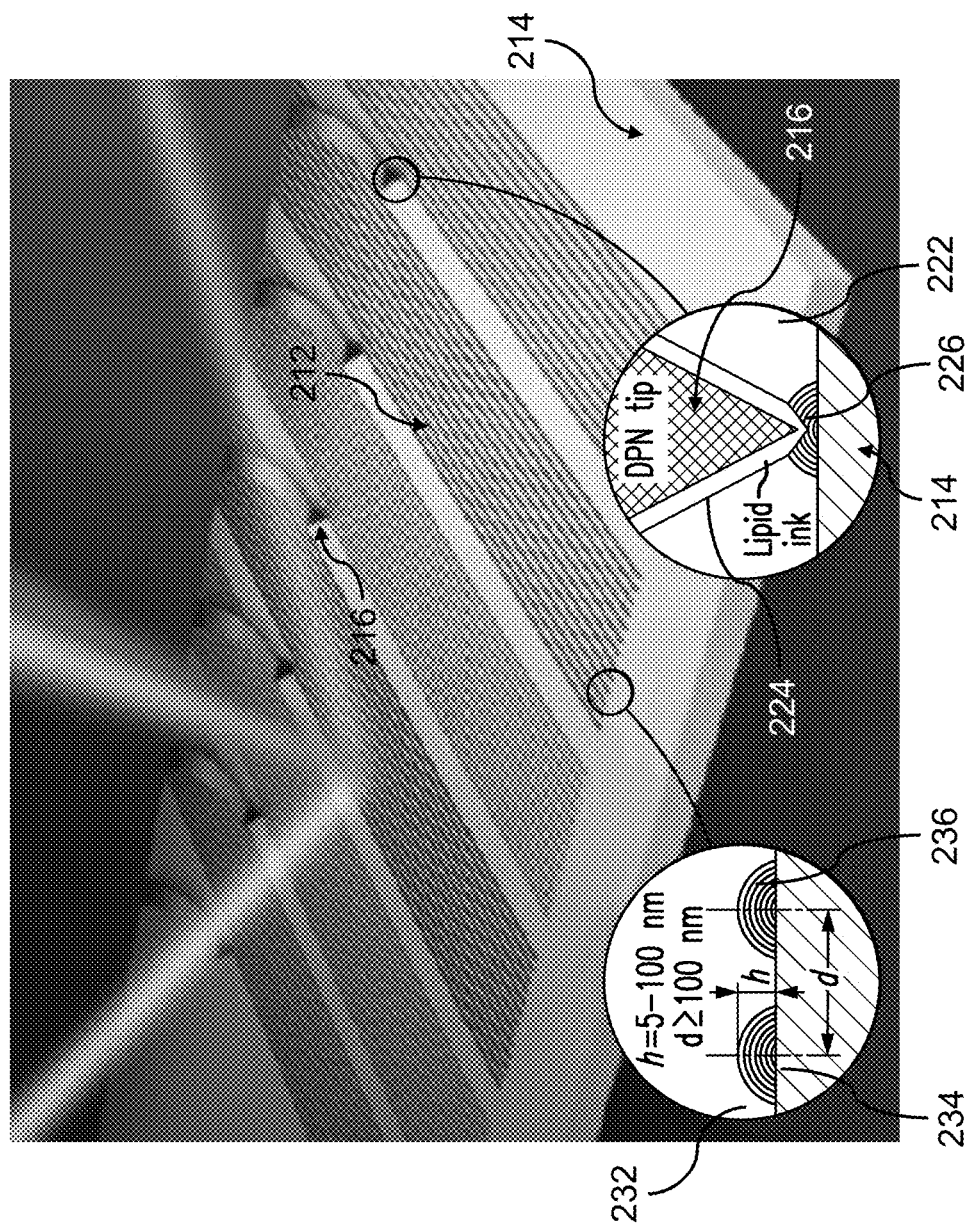
FIG. 2 is a schematic drawing of a technique according to one embodiment of the present invention that may be used to fabricate lipid multilayer gratings.

The sensors of the present invention may be made up of various lipids using DPN techniques. For example, fluid phospholipids such as 1,2-dioleoyl-sn-glycero-3-phosphocholine (DOPC) are particularly well suited as biocompatible inks for DPN because of their viscosity, and corresponding properties of ink transport between the DPN tip and substrate, may be readily tuned by the relative humidity, Lenhert, S., Sun, P., Wang, Y. H., Fuchs, & Mirkin, C. A. Massively parallel dip-pen nanolithography of heterogeneous supported phospholipid multilayer patterns. Small 3, 71-75 (2007), the entire contents and disclosure of which are incorporated herein by reference. Fluid phospholipids may therefore be used to write on a variety of solid substrates, both smooth surfaced and pre-patterned, without a specific chemical driving force or covalent binding to the surface. Because fluid phospholipids are biological molecules, a variety of functional membrane lipids (both natural and synthetic) are readily available and can be directly dispersed in the ink for the fabrication of biofunctional structures. These different biofunctions may then be simultaneously written onto the same substrate using different tips in a parallel array, for example, by microfluidic inkwells or inkjet printing, a method referred to as multiplexed DPN, see Wang, Y. et al. A self-correcting inking strategy for cantilever arrays addressed by an inkjet printer and used for dip-pen nanolithography. Small 4, 1666-1670 (2008), and Sekula, S. et al. Multiplexed lipid dip-pen nanolithography on subcellular scales for the templating of functional proteins and cell culture. Small 4, 1785-1793 (2008), the entire contents and disclosures of which are incorporated herein by reference. Importantly, the self-organization properties of phospholipids enable them to stack controllably into multilayer structures that are used for optical scattering, as shown schematically in FIG. 2. FIG. 2 shows lipid multilayer gratings 212 deposited on a substrate 214 using DPN tips 216. An inset 222 shows a DPN tip 216 and lipid ink 224 being deposited as a line 226 of one of lipid multilayer gratings 212. Inset 232 shows two lines, i.e., lines 234 and 236, of one of arrays 212.

As shown in FIG. 2, parallel DPN tip arrays are used to deposit multiple lipids simultaneously with controllable multilayer heights, laterally structured to form arbitrary patterns such as diffraction gratings with feature sizes on the same scale as UV, visible or infrared light. In situ observation of the light diffracted from the patterns may be carried out during DPN and used for high-throughput optical quality control without the need for fluorescence labels.

The ability of lipid DPN to control the lipid multilayer height constructively is important to forming multilayer structures. With the exception of capillary assembly, the majority of lipid patterning methods are limited to single monolayers or surface-supported lipid bilayers.

Figure 3:
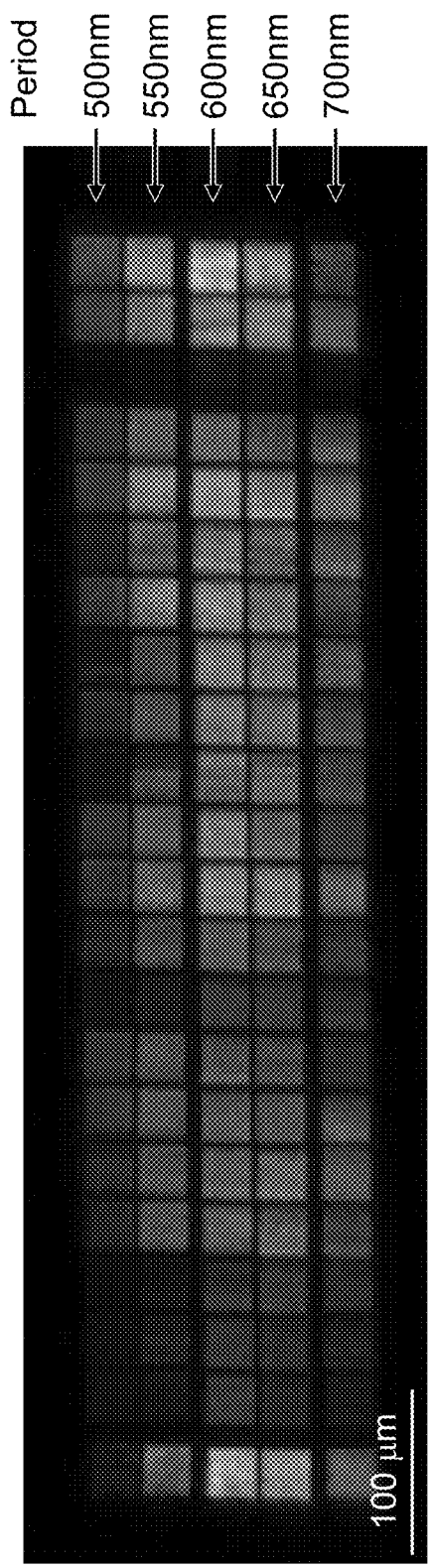
FIG. 3 is an optical micrograph of light diffracted from gratings of different periods that were fabricated in parallel with a one-dimensional tip array on a poly(methyl methacrylate) (PMMA) surface.

The quality of the structure can be rapidly characterized by illumination of the patterns in a way that allows observation of the light scattering from gratings over large areas, which may also be carried out in situ during DPN fabrication, allowing rapid prototyping of photonic structures. For example, in FIG. 3, the period of the gratings is varied between 500 and 700 nm, and the diffracted light of different colors was detected by a simple charge-coupled device (CCD) camera. Although not visible in FIG. 3, the gratings having a period of 500 nm are blue in color, the gratings having a period of 550 nm are blue-green in color, the gratings having a period of 600 nm are yellow in color, the gratings having a period of 650 nm are orange in color and the gratings having a period of 700 nm are red in color. FIG. 3 is an optical micrograph of light diffracted from gratings of different periods that were fabricated in parallel with a one-dimensional tip array on a poly (methyl methacrylate) (PMMA) surface. Each tip wrote five gratings with periods ranging from 500 to 700 nm in steps of 50 nm (top to bottom).

The different colors observed in FIG. 3 (shown in grayscale) as a function of grating pitch are described by the grating equation $d(\sin\theta_m + \sin\theta_i) = m\lambda$, where d is the period of the grating, $\theta_m$ and $\theta_i$ are the angles of diffraction maxima and incidence, respectively, m is the diffraction order, and $\lambda$ the wavelength of light. Using white light as incident light, the intensity of light is observed at $\theta m \approx 0°$ normal to the grating plane. The color observed depends only on the grating period and $\theta_i$, which is adjusted to give optimal contrast with a period of 600 nm illuminated at $\theta_i \approx 70°$.

Correlating the grating topographies measured by atomic force microscopy (AFM) with the intensity of light diffracted from iridescent gratings into the camera permits calibration of the observed diffraction intensities as shown in FIGS. 4 and 5. FIG. 4 is an AFM topographical image of an iridescent grating with a period of 600 nm and height of (29+3) nm. FIG. 5 is a graph showing the correlation between the iridescent grating heights (measured by AFM) and the measured intensity of light diffracted from iridescent gratings with a period of 600 nm. The grating efficiency steadily increases linearly to heights of (50+10) nm, after which the multilayer patterns fuse to form a continuous film that no longer diffracts light. A line is fit to the linear region of the data and can be used for optical calibration of the heights. Error bars for the height measurement represent the standard deviation in heights between different grating lines. FIG. 6 is an optical micrograph of the diffraction from the gratings in FIG. 5 and their measured AFM heights. FIG. 5 shows that, for gratings with a period of 600 nm and ink composed of the pure DOPC, the intensity of diffracted light increases linearly with grating height up to 40-60 nm then discontinuously drops off for thicker gratings, because beyond that height, the grating lines fuse together to form a continuous film. The variation in height along a single line is ~10% of the grating height. In one embodiment of the present invention, a graph similar to the graph shown in FIG. 5 may be used in preparing a calibration profile based on light diffracted by iridescent microstructures as described in more detail below.

Figure 7:
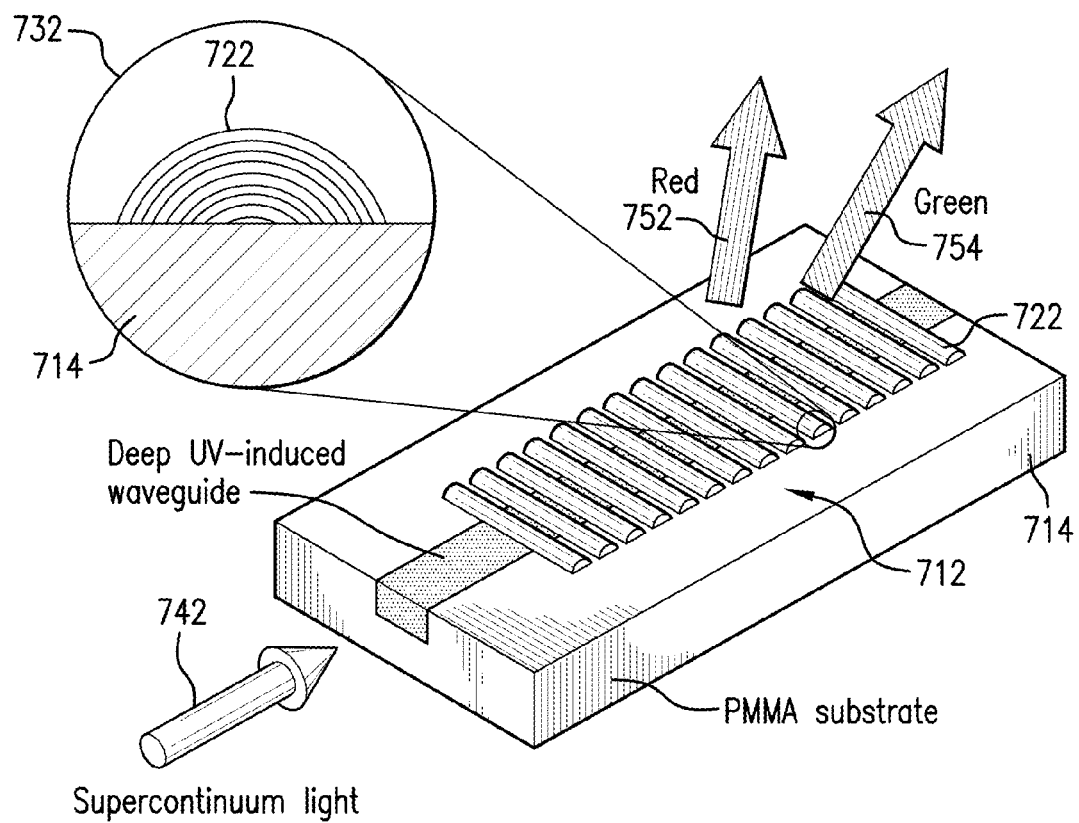
FIG. 7 is a schematic drawing of waveguide grating couplers according to one embodiment of the present invention.

The constructive and parallel nature of DPN makes this technique capable of integrating multiple materials on surfaces that have been pre-structured by top-down lithographic methods for complex device fabrication. As an example, functional waveguide grating coupler as described in Tamir, T. & Peng, S. T. Analysis and design of grating couplers. Appl. Phys. 14, 235-254 (1977), the entire contents and disclosure of which are incorporated herein by reference may be fabricated by direct DPN patterning of DOPC multilayer gratings onto waveguides as shown in FIG. 7. In FIG. 7, the light of a supercontinuum laser source is coupled into a single-mode strip waveguide and decoupled by the waveguide grating coupler, which is a grating-based device that couples light in and/or out of a waveguide.

FIG. 7 shows a lipid multilayer grating 712 on a substrate 714. Lipid multilayer grating 712 acts as a grating coupler. Lipid multilayer grating 712 is comprised of lines 722, one of which is shown in greater detail in inset 732. As shown in FIG. 7, light 742 of a supercontinuum laser source (not shown) is coupled into a single-mode strip waveguide 744 and decoupled by grating 712. Red light 752 and green light 754 are shown being scattered by grating 712.

Figure 8:
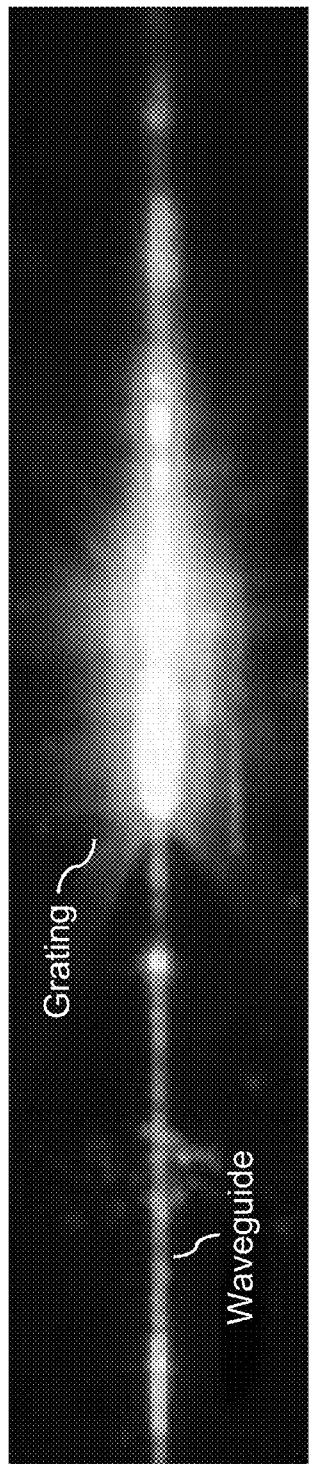
FIG. 8 is a photograph of a waveguide grating coupler according to one embodiment of the present invention at 30° from the surface normal.
Figure 9:
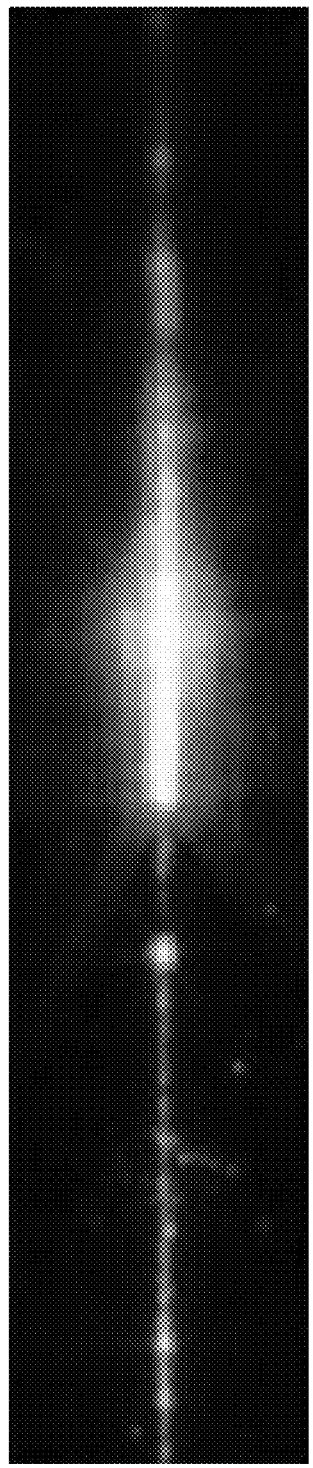
FIG. 9 is a photograph of a waveguide grating coupler according to one embodiment of the present invention at 45° from the surface normal.

According to one embodiment of the present invention, waveguides have been formed on PMMA surfaces by exposure to deep ultraviolet light through a chromium mask, as described in Henzi, P., Rabus, D. G., Bade, K., Wallrabe, U. & Mohr, J. Low cost single mode waveguide fabrication allowing passive fiber coupling using LIGA and UV flood exposure. Proc. SPIE 5454, 64-74 (2004), the entire contents and disclosure of which are incorporated herein by reference. A lipid grating with a period of 700 nm was defined on top of the UV-induced PMMA waveguide with the lines perpendicular to the waveguide. Light from a supercontinuum laser source (Koheras SuperK Versa) with a spectral emission range of $\lambda$=500-800 nm was coupled into the waveguide through an optical fiber. Supercontinuum laser light of different wavelengths was decoupled under different angles by the grating coupler, as shown in FIGS. 8 and 9. FIGS. 8 and 9 are photographs of the coupler at 30° and 45°, respectively, from the surface normal, where the red and green portions of the guided supercontinuum light are coupled to radiation modes. Although not visible in FIGS. 8 and 9, the grating of FIG. 8 is green in color and the grating of FIG. 9 is red in color.

Figure 10:
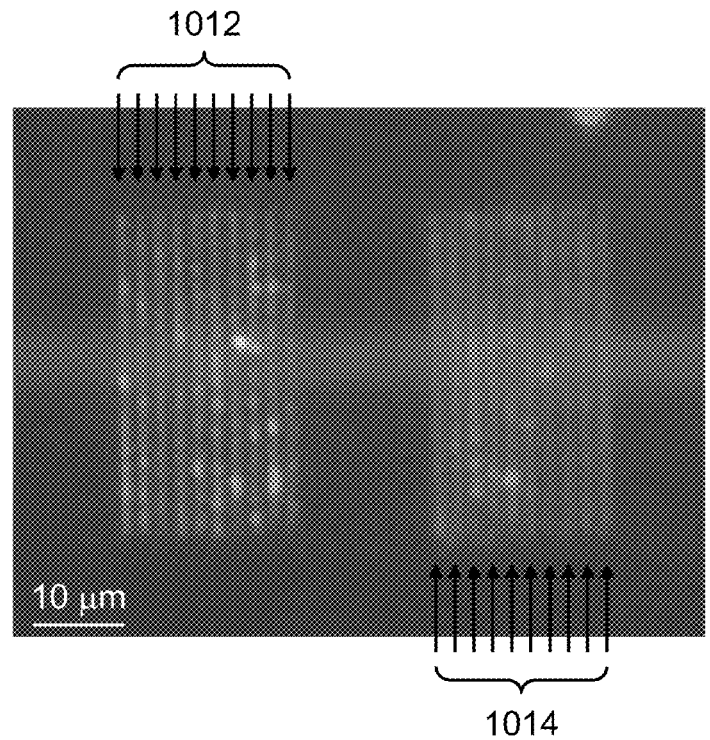
FIG. 10 is an image of red and green fluorescence for two different gratings according to one embodiment of the present invention.
Figure 11:
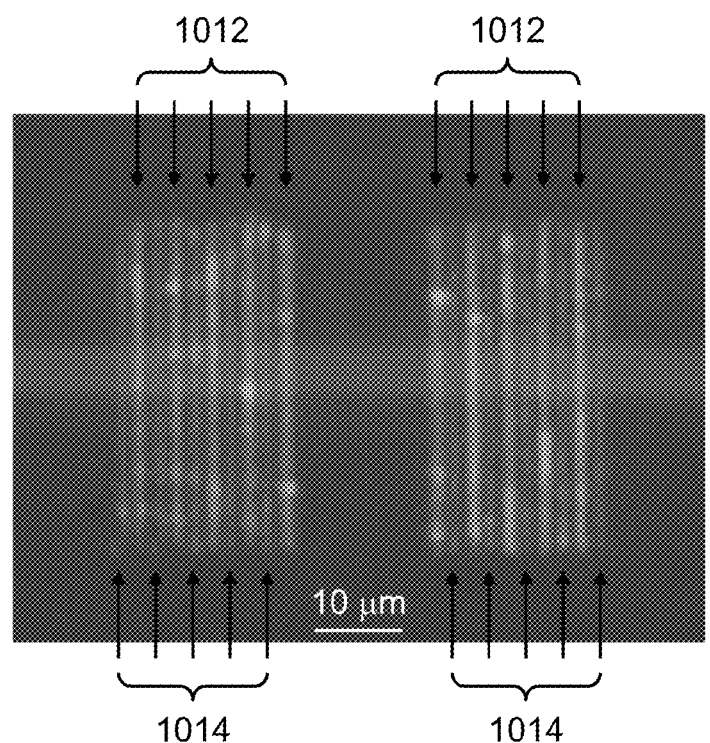
FIG. 11 is an image showing two gratings where the individual elements within a single grating are composed of alternating materials.

Advanced photonics applications demand the integration of multiple functional materials on microscopic and nanoscopic scales and in arbitrary geometries. To demonstrate the qualitatively unique ability of DPN to address this challenge, multiplexed DPN as described in Sekula, S. et al. Multiplexed lipid dip-pen nanolithography on subcellular scales for the templating of functional proteins and cell culture. Small 4, 1785-1793 (2008), the entire contents and disclosure of which are incorporated herein by reference, was used to write two different fluorescently labeled lipids simultaneously on pre-structured waveguides. FIGS. 10 and 11 show a fluorescence overlay of red and green fluorescence from two different fluorescently labeled lipids (red and green vertical lines) integrated with a pitch of 2 μm by DPN patterning on a waveguide (a horizontal thick gray line is visible in FIGS. 10 and 11 because of autofluorescence). In particular, FIG. 10 shows two different gratings simultaneously fabricated from two different tips in a parallel array dipped in inks doped with 1 mol % of fluorescently labeled lipids—rhodamine (red), indicated by arrows 1012, and fluorescein (green), indicated by arrows 1014. FIG. 11 shows two more gratings made with the same tip array and inks, where the individual elements within a single grating are composed of alternating materials. This capability of DPN to control the placement of different materials selectively within a structure opens new possibilities for the rapid prototyping and fabrication of multicomponent photonic structures.

The structuring of lipids into photonic structures provides a label-free method of observing dynamic structural changes in the lipid multilayer morphologies. These changes may be understood in terms of liquid adhesion to a solid surface where the lipid multilayers are, essentially, structured microscopic and nanoscopic oil droplets adherent on a surface. Three examples of shape changes are spreading, dewetting and intercalation of materials into the multilayer structure, as schematically illustrated in FIG. 12. In FIG. 12, lipid layers are indicated by reference number 1212, protein layers by reference number 1214, and a substrate by reference number 1216. FIG. 12A shows lipid layers 1212 deposited as a multilayer on substrate 1216. FIG. 12B shows spreading of lipid layers 1212 on substrate 1214. FIG. 12C shows dewetting of lipid layers 1212 with a covering of a protein layer 1214. FIG. 12D shows intercalation of protein layers 1214 with lipid layers 1212.

The drawings A, B, C and D of FIG. 12 have been sketched to reflect the well-documented tendency for hydrated phospholipid multilayers to stack on surfaces into ordered multilamellar bilayer stacks and for hydrophilic materials, such as proteins, to intercalate themselves between the hydrophobic multilayer sheets.

Figure 13:
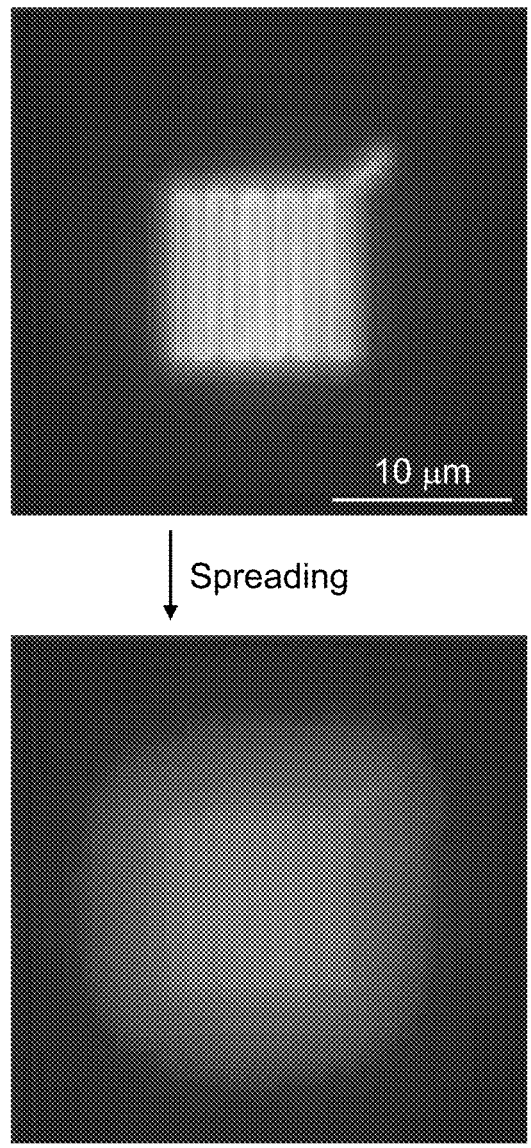
FIG. 13 is a fluorescence micrograph showing spreading of a lipid in air after 5 minutes of exposure to humidity above 40%.

When patterned on surfaces, lipid multilayers are known to spread spontaneously in aqueous solution to form lipid bilayer or monolayer precursor films on certain substrates; see Lenhert, S., Sun, P., Wang, Y. H., Fuchs, H. & Mirkin, C. A. Massively parallel dip-pen nanolithography of heterogeneous supported phospholipid multilayer patterns. *Small* 3, 71-75 (2007), Sanii, B. & Parikh, A. N. Surface-energy dependent spreading of lipid monolayers and bilayers. Soft Matter 3, 974-977 (2007); Nissen, J., Gritsch, S., Wiegand, G. & Radler, J. O. Wetting of phospholipid membranes on hydrophilic surfaces-concepts towards self-healing membranes. *Eur. Phys. J. B* 10,335-344 (1999); Radler, J., Strey, H. & Sackmann, E. Phenomenology and kinetics of lipid bilayer spreading on hydrophilic surfaces. *Langmuir* 11, 4539-4548 (1995), the entire disclosures and contents of which are incorporated herein by reference. In air, the phospholipid DOPC undergoes a hydration-induced gel-fluid phase transition at a relative humidity of 40%, as observed by humidity-controlled calorimetry and DPN; see Lenhert, S., Sun, P., Wang, Y. H., Fuchs, H. & Mirkin, C. A. Massively parallel dip-pen nanolithography of heterogeneous supported phospholipid multilayer patterns. Small 3, 71-75 (2007); Sanii, B. & Parikh, A. N. Surface-energy dependent spreading of lipid monolayers and bilayers. Soft Matter 3, 974-977 (2007); and Ulrich, A. S., Sami, M. & Watts, A. Hydration of DOPC bilayers by differential scanning calorimetry. *BBA Biomembranes* 1191, 225-230 (1994), the entire contents and disclosures of which are incorporated herein by reference. The multilayer gratings therefore remain stable for long-term storage at low humidity, but upon exposure to humidity higher than 40% in air, the multilayers become hydrated and fluid and therefore slowly spread on the surface. This spreading can be observed both by fluorescence microscopy as shown in FIG. 13 and as a decrease in the diffraction intensity irreversibly indicating the presence of water vapor above 40% humidity. FIG. 13 is a fluorescence micrograph made with fluorescently labeled materials of lipid spreading in air after 5 minutes of exposure to humidity above 40%.

Figure 14:
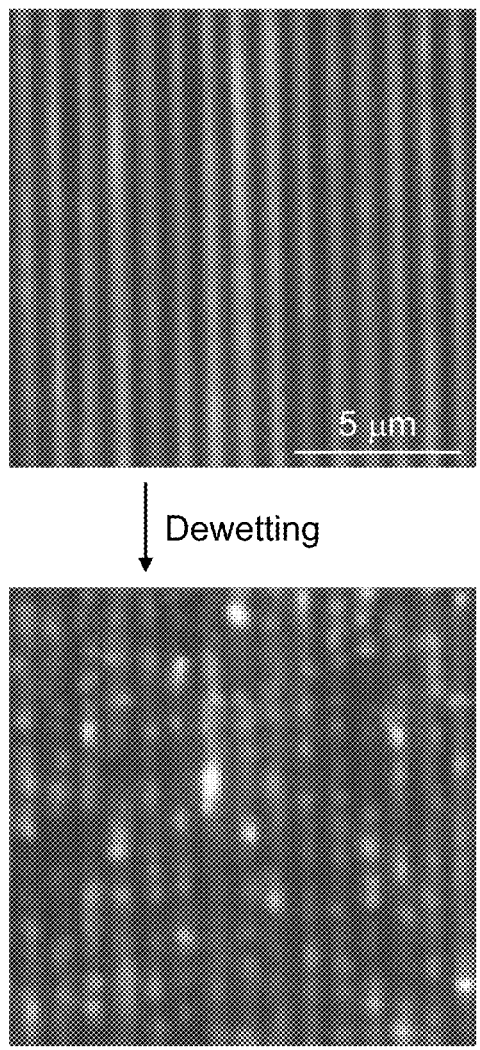
FIG. 14 is a fluorescence micrograph showing dewetting of smooth lines of biotin-containing gratings under solution to form droplets after 1 minute of exposure to the protein streptavidin.
Figure 15:
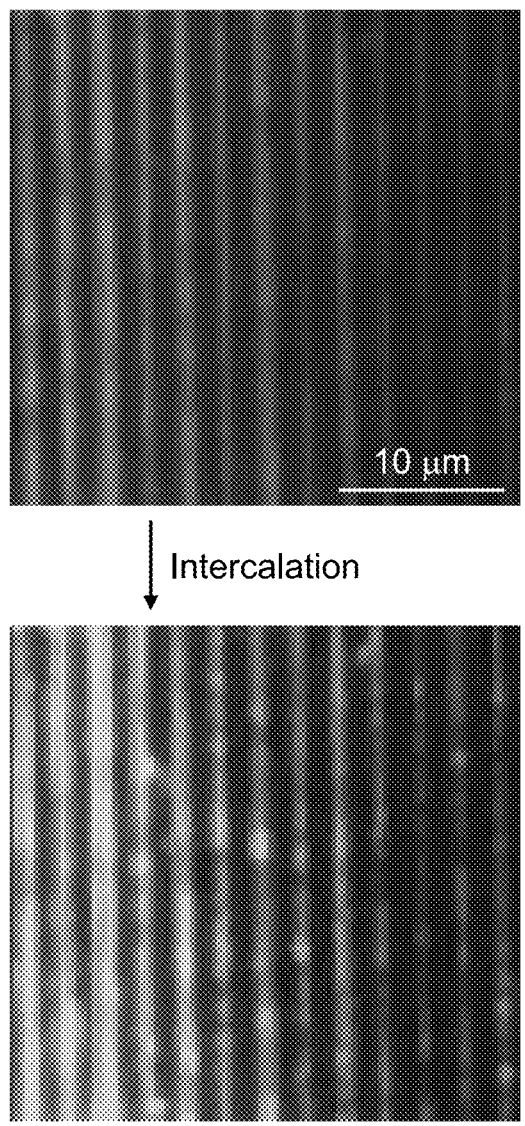
FIG. 15 is a fluorescence micrograph showing intercalation of protein into lipid multilayer grating lines of different heights after 1 hour.

Surprisingly, lipid multilayer gratings can remain stable in aqueous solution for at least several days when immersed under the appropriate conditions, permitting study of the structural changes upon binding of biological molecules such as proteins, which causes the dewetting and intercalation effects observed by fluorescence microscopy and shown in FIGS. 14 and 15. FIG. 14 is a fluorescence micrograph made with fluorescently labeled materials of dewetting of smooth lines of biotin-containing gratings under solution to form droplets after 1 minute of exposure to the protein streptavidin. FIG. 15 is a fluorescence micrograph made with fluorescently labeled materials of intercalation of protein into lipid multilayer grating lines of different heights after 1 hour. The top image is a fluorescence micrograph of fluorescein-(green) labeled lipid grating lines before exposure to protein, and the bottom image shows an image of both red and green fluorescence channels overlaid after binding of a Cy3-(red) labeled protein bound to the layers. Intercalation is indicated because the intensity of fluorescence from bound protein is proportional to the height of the lipid multilayer.

Figure 16:
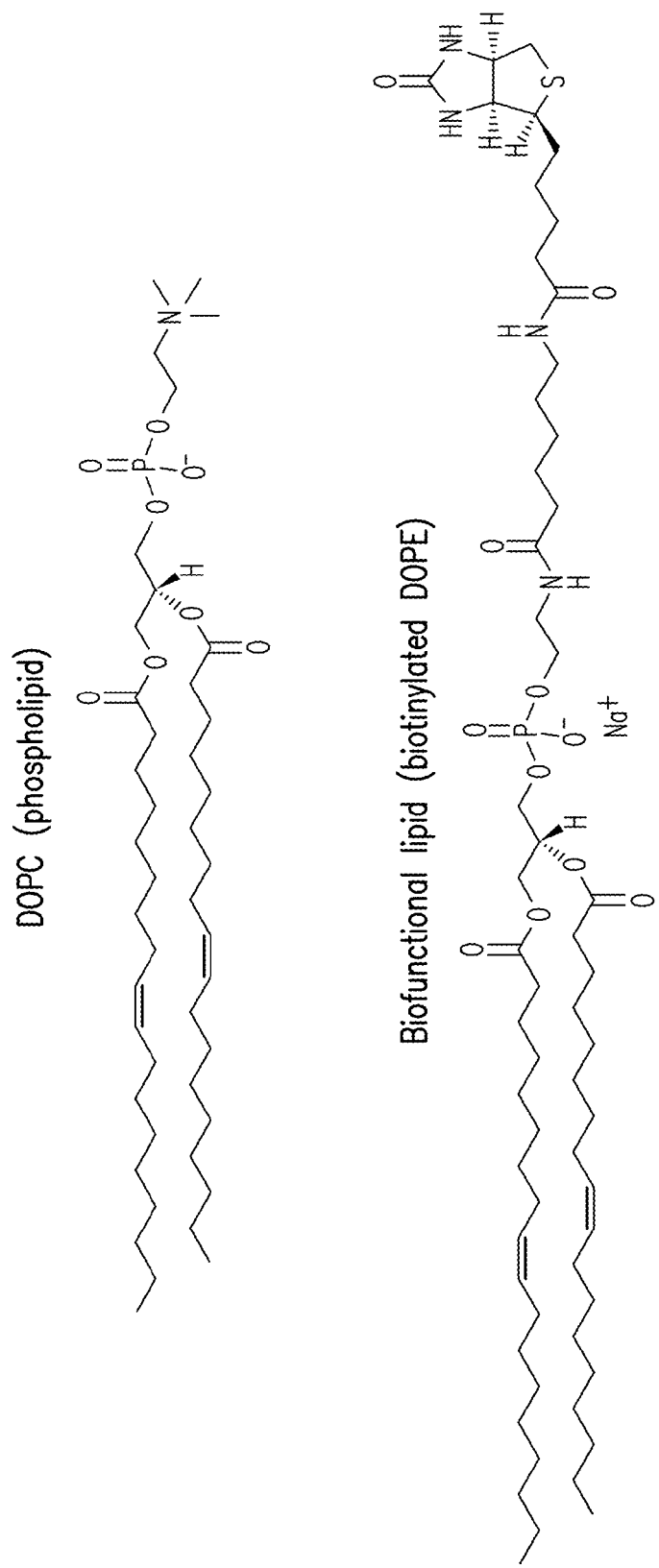
FIG. 16 shows the chemical structures of 1,2-dioleoyl-sn-glycero-3-phosphocholine (DOPC), a phospholipid, and 1,2-dioleoyl-sn-glycero-3-phosphoethanolamine-N-(lissamine rhodamine B sulfonyl) (DOPE-RB) used to make lipid multilayer gratings according to one embodiment of the present invention.

To observe the dewetting and intercalation effects using fluorescence microscopy, DOPC ink was doped with 5 mol % of a biotinylated lipid. The chemical structures of these lipids, i.e., phospholipids (1,2-dioleoyl-sn-glycero-3-phosphocholine (DOPC) and the biotinylated lipid 1,2-dioleoyl-sn-glycero-3-phosphoethanolamine-N-(cap biotinyl)), are shown in FIG. 16. Fluorescently labeled lipids reveal the multilayer grating lines to break into droplets upon exposure to 50 nM of the tetravalent biotin-binding protein streptavidin. Such dewetting or formation of droplets from a continuous line drawn on a surface by a pen is a common practical method of characterizing surface energies by means of dyne pens, see Rentzhog, M. & Fogden, A. Print quality and resistance for water-based flexography on polymer-coated boards: dependence on ink formulation and substrate pretreatment. *Prog. Org. Coat.* 57, 183-194 (2006), the entire contents and disclosure of which is incorporated herein by reference. In the present case, this method extended to the nanoscale.

Using both fluorescently labeled proteins and lipids, it was possible to observe intercalation of the proteins into lipid multilayers. For example, in the experiment shown in FIG. 1, lines of different multilayer heights were drawn with DOPC containing both a fluorescein-labeled lipid and a biotinylated lipid, as indicated by the different intensities of the fluorescence from the different lines in the green, 'before' image of FIG. 16. Upon binding of Cy3-labeled protein (red and green overlay image in FIG. 15), the higher lines can be seen to be significantly brighter than the lower lines, suggesting intercalation into the multilayers after an incubation period of one hour. Further experiments using fused biotinylated squares of different heights to bind streptavidin, as well as the use of his-tagged green fluorescent protein (GFP) to bind to gratings doped with his-tag binding lipids, confirm the ability of proteins to intercalate themselves within the multilayers.

The tendency for the lipid grating elements to change size and shape upon protein binding, in combination with their optical properties and innate biofunctions, opens the possibility of a new, biologically inspired mechanism for label-free protein detection. Grating-based biosensors are well established and typically function by detecting a spectral change upon analyte binding to the surface of a biofunctionalized solid grating. Although the vast majority of such sensors are made of solid materials, liquid diffraction gratings formed from the directed condensation of water droplets onto chemically patterned surfaces have been proposed as humidity sensors as well as for fundamental studies in adhesion science. The lipid gratings according to one embodiment of the present invention differ from the existing grating-based sensors described above in two aspects. First, the biofunctions may be incorporated directly into the phospholipid ink, eliminating the need for further biofunctionalization steps of the transducer as in the case of existing solid gratings. Second, in contrast to the condensation-based liquid gratings, the immiscibility of the adherent liquid phospholipid droplets with water permits studies in biologically relevant aqueous solutions. Procedures for making condensation-based liquid gratings are described in Kumar, A. & Whitesides, G. M. Patterned condensation figures as optical diffraction gratings. Science 263, 60-62 (1994), the entire contents and disclosure of which are incorporated herein by reference.

Figure 17:
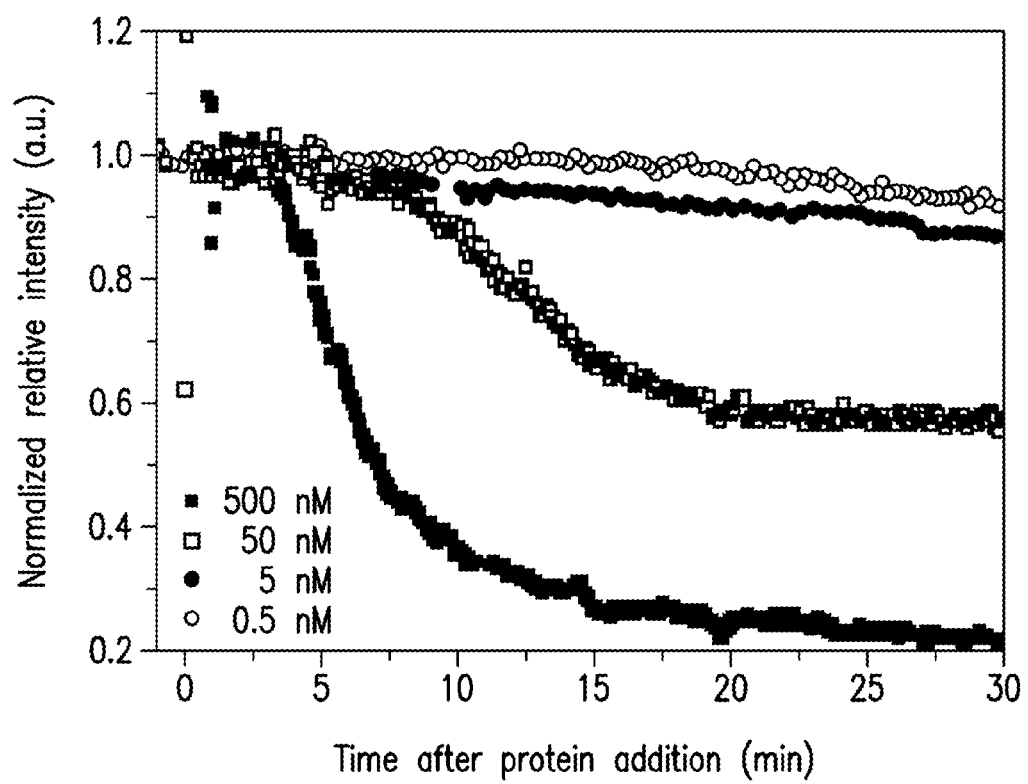
FIG. 17 is a graph showing label-free detection of protein binding by monitoring of the diffraction from gratings upon exposure to protein at different concentrations.

Monitoring the intensity of light diffracted from lipid multilayer gratings upon exposure to analytes permits optical detection of protein binding without any fluorescent labels. For example, FIG. 17 shows the optical response of biotinylated gratings upon exposure to streptavidin protein at different concentrations. The decrease in intensity is due to the dewetting mechanism, which results in a lower diffraction efficiency. The observed limit of detection of 5 nM after 15 minutes is comparable to that of solid grating-based sensors, which are typically diffusion limited at concentrations on the order of ~5 nM, but after incubation for 90 minutes, it is possible to observe significant dewetting of biotinylated gratings, as compared to the pure DOPC control gratings, at a protein concentration of 500 pM. As the dewetting detection mechanism depends on a change in surface energy, the sensitivity for a particular analyte may be optimized by adjustment of the sensitivity of the membrane tension to ligand binding, as is the case in many cell-signalling processes and model membrane systems as described in Chiu, D. T. et al. Chemical transformations in individual ultrasmall biomimetic containers. Science 283, 1892-95 (1999), the entire contents and disclosure of which are incorporated herein by reference. Furthermore, phospholipid bilayers are highly resistant to nonspecific protein binding, and it is therefore possible to carry out the same detection of protein added to fetal calf serum. The response of the grating to protein binding depends on the grating height; higher gratings give the best response for protein detection at low concentration. Therefore, observing a quantitative concentration-dependent response requires using gratings of equivalent height (35+5 nm as determined by diffraction intensity calibration) for the experiment series shown in FIG. 17.

Intercalation effects may also be observed by monitoring of diffraction which correspond to increases in the grating volume and therefore height. For example, in the case of streptavidin binding, dewetting and intercalation are observed simultaneously for higher gratings at higher concentrations (for example, 500 nM and above), whereas only intercalation is observed for the lower gratings (for example, FIG. 15). At lower streptavidin concentrations, however, no response is observed for lower gratings, and only dewetting is observed for the higher gratings. Another demonstration of intercalation may be observed by diffraction on binding of a his-tagged GFP protein to nickel-chelating lipid gratings, where the diffraction intensity doubled. Upon addition of imidazole, which releases the his-tag-bound protein, the diffraction intensity could be seen to decrease, and the effect was reversible. Although intercalation and reversibility of the fluid grating response to analytes has so far been observed only for higher, millimolar concentrations, where new sensor constructs are hardly needed, the intercalation mechanism demonstrates the possibility of expanding the dynamic range of disposable sensors. Furthermore, the ability to observe analyte intercalation and desorption from lipid multilayers provides a new, label-free method of characterizing loading and release conditions of liposomes for delivery and nanoscale chemistry applications.

In one embodiment, the present invention provides a process for the fabrication of photonic structures composed of phospholipid multilayers. In one embodiment, the fabrication process of the invention allows direct writing of arbitrary patterns, composed of multiple biocompatible membrane-based materials, on a variety of surfaces, including pre-patterned substrates. The technique is useful for high-throughput biophysical analysis with lipid-based photonic structures and novel photonic sensing elements capable of label-free biosensing by means of a dynamic shape change upon analyte binding. Higher gratings that respond to analyte binding by a surface-tension change are found to be suitable for detection of analytes at low concentrations, whereas mechanisms based on intercalation of materials into the fluid gratings may expand the dynamic range of sensing as well as provide a new way to probe dynamic biomembrane function. The bottom-up fabrication method and unique biophysical properties of nanostructured lipid multilayers permits the integration of complex and dynamic biophotonic circuits.

In another embodiment, the present invention provides the formation of printed cellular microarrays on chips to enable systematic studies of the molecular and geometric mechanisms of intercellular communication in quorum sensing. In yet another embodiment, the present invention provides the development of semi-synthetic cell-based sensors capable of environmental monitoring.

Figure 18:
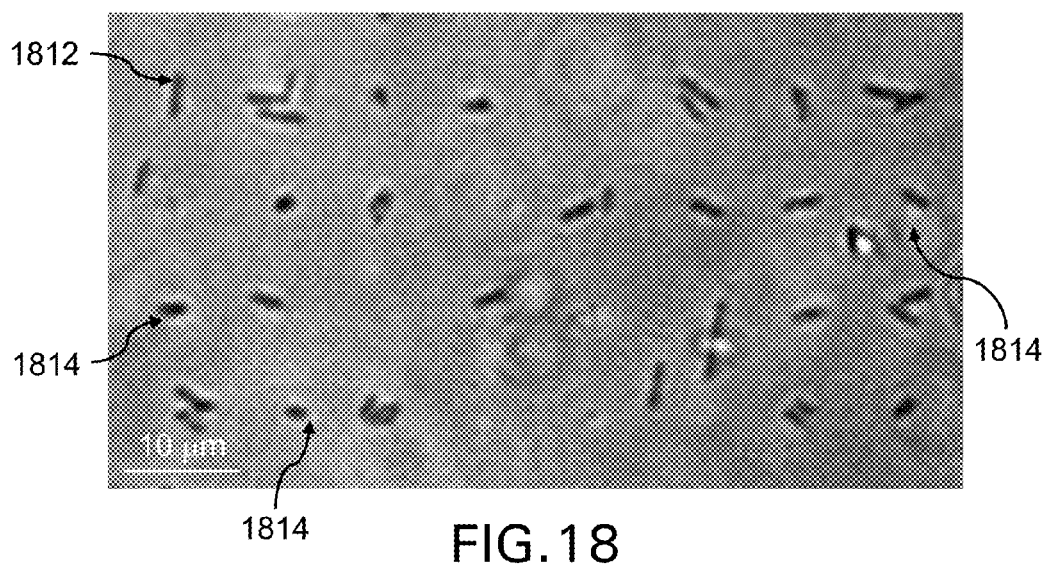
FIG. 18 is an optical micrograph of $E.\ coli$ cells selectively adhered to a fluorescently labeled lipid microarray.

In one embodiment, each sensor of an array of sensors may have bound to, complexed with, encapsulated in, inserted in, etc. each of the lipid multilayer structures of the array a reactive agent such as living bacteria, as shown in FIG. 18.

In one embodiment, the present invention provides a method of monitoring the optical response of lipid multilayer gratings. For this purpose, the gratings may be loaded with different functional groups, antibodies and signaling molecules known to influence quorum sensing and the diffracted light will be quantified as the grating arrays are exposed to different bacterial strains. When a cell attaches to a grating, an optical response is expected, allowing label-free detection of the bacteria. Antibodies will allow detection and selective attachment of target bacterial strains, while the presence of functional groups and signaling molecules in the gratings will allow systematic investigation of how quorum sensing molecules affect cells in a confined environment. FIG. 18 shows how living bacteria may be bound to an array of sensor elements. FIG. 18 is an optical micrograph of *E. coli* cells 1812 selectively adhered to a fluorescently labeled lipid microarray 1814 (lighter dots). In the experiment shown in FIG. 18, motile *E. coli* bacteria cells adhere selectively to certain types of phospholipids.

In one embodiment of the present invention, the lipid multilayer gratings may be made from a mixture of two different lipids. In one embodiment of the present invention, two or more lipid multilayer gratings of a device of the present invention may be made from a different lipid or a different mixture of lipids.

In one embodiment of the present invention, the lipid multilayers may serve as models for organic contaminants, as well as model eukaryotic cells, and the bacterial strains will be selected accordingly. Bacterial gene expression may be monitored using cells modified with suitable reporter genes, and mutant strains will be identified by exposure to ionizing radiation and sequencing.

In one embodiment, the present invention provides surface-based arrays composed of different bacterial strains, possibly encapsulated in a lipid matrix in order to allow control of the gene expression of the cells. The bacteria may be purified and mixed with the phospholipid inks prior to DPN printing and deposited in a parallel and multiplexed manner. Cells expressing fluorescent proteins may be used to identify the conditions for printing individual, as well as multiple, cells within each spot. The arrays may then be incubated and the proliferation of the cells monitored by fluorescence measurements in real time. Because DPN allows precise control of spot volume and spacing, the communication between cells in neighboring dots will be studied as a function of dot spacing and size.

In one embodiment, the present invention provides label-free biosensors capable of environmental monitoring. In one embodiment of the present invention, one type of biosensor may be able to identify the different types of bacteria within a population by measuring the specific binding to the arrays. In another embodiment of the present invention, a second type of sensor may contain living bacteria, which will, upon addition of an analyte (e.g. environmental water samples) respond to the presence of materials in the sample as the lipid-encapsulated bacteria interact with the sample and the other bacteria on the chip. The chips may then be used to analyze liquid as well as atmospheric samples, as the cells will be trapped within lipid vesicles on the surface. After calibrating these chips with known standards, the structure-dependant optical properties of these arrays may provide a versatile and sensitive system based on live yet captive and well organized cells for environmental monitoring.

In one embodiment, the present invention provides a lab-on-a-chip device for mobile multiplexed blood analysis. In another embodiment, the present invention provides a lab-on-a-chip device for screening how different microbes and microbe populations metabolize different oils. Identification of such microbe populations may be useful for environmental monitoring, oil spill cleanup and natural bioremediation.

In one embodiment, the present invention provides in situ detection and control of bacterial quorum sensing based on optical diffraction from nanostructured lipid multilayer gratings. In one embodiment, the present invention provides semi-synthetic cell-based quorum sensors and a quorum sensor system capable of environmental monitoring such as the detection of analytes and bacterial strains in complex mixtures.

Figure 19:
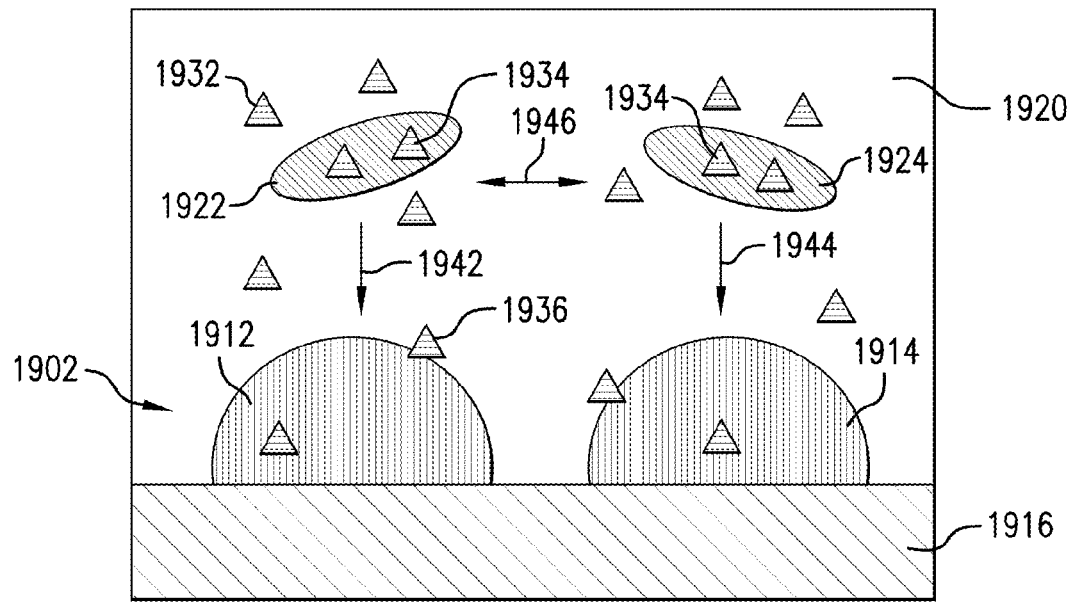
FIG. 19 is a schematic diagram showing a lipid multilayer grating being used to detect the effect of quorum sensing in bacteria in an aqueous solution according to one embodiment of the present invention.

FIG. 19 shows a method according to one embodiment of the present invention for detecting the effects of quorum sensing of free-floating bacteria on a lipid multilayer grating according to one embodiment of the present invention. Lipid multilayer grating 1902 of FIG. 19 comprises a series of lines, two of which are shown in FIG. 19, i.e., lipid multilayer line 1912 and lipid multilayer line 1914 that have been deposited on a substrate 1916 using a process such as DPN. Lipid multilayer line 1912 and lipid multilayer line 1914 are exposed to an aqueous solution 1920 that contains bacteria 1922 and bacteria 1924 and quorum sensing molecules 1932 (shown as triangles). Some quorum sensing molecules 1932 are bound to or encapsulated within bacteria 1922 and 1924 as shown by reference character 1934 and some of sensing molecules 1932 bind to lipid multilayer lines 1912 and 1914 as indicated by reference character 1936. Bacterium 1922 interacts with lipid multilayer line 1912 as indicated by arrow 1942. Bacterium 1924 interacts with lipid multilayer line 1914 as indicated by arrow 1944. Bacteria 1922 and 1924 also interact with each other as indicated by double-headed arrow 1946.

Although one type of array of lipid multilayer structures, i.e., lines, are shown in FIG. 19, the lipid multilayer structures of FIG. 19 may be any shape.

In one embodiment of the present invention, by detecting changes in the light scattered by the lines of the array of FIG. 19, it is possible to determine the affect of quorum sensing molecules on an array of lipid multilayer structures. If the lipid multilayer structures are fluorescent, changes in the intensity of emitted fluorescent light may be detected to determine the effect of quorum sensing molecules on an array of lipid multilayer structures. Such information may be useful in providing baseline data when lipid multilayer structures are used in quorum sensors.

Figure 20:
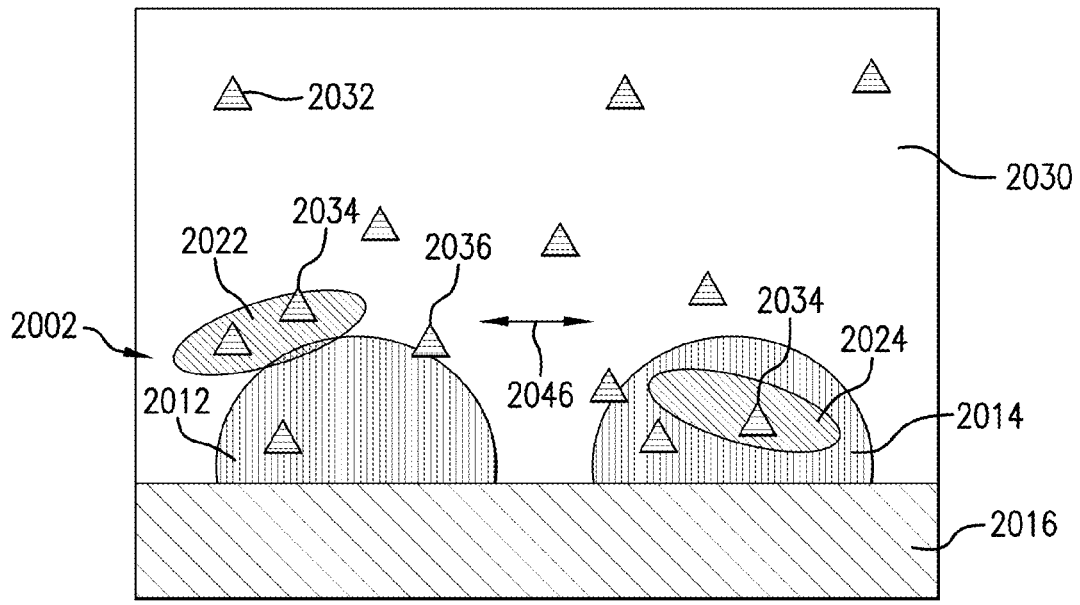
FIG. 20 is a schematic diagram showing a quorum sensor array according to one embodiment of the present invention.

FIG. 20 shows a method for detecting the effects of quorum sensing by bacteria bound to or encapsulated within the lipid multilayer structures of a lipid multilayer grating according to one embodiment of the present invention. The bacteria bound to the lipid multilayer grating form a quorum sensory array 2002. The lipid multilayer grating of quorum sensor array 2002 comprises a series of lines, two of which are shown in FIG. 20, i.e., lipid multilayer line 2012 and lipid multilayer line 2014 that have been deposited on a substrate 2016 using a process such as DPN. A bacterium 2022 is bound to or encapsulated within lipid multilayer line 2012 and together form a first quorum sensor. A bacterium 2024 is bound to or encapsulated within lipid multilayer line 2014 and together form a second quorum sensor. An aqueous solution 2030 containing quorum sensing molecules 2032 (shown as triangles) surround the first and second quorum sensor. Some quorum sensing molecules 2032 are bound or encapsulated within bacteria 2022 and 2024 as shown by reference character 2034 and some quorum sensing molecules 2032 bind to lipid multilayer lines 2012 and 2014 as indicated by reference character 2036. Bacteria 2022 and bacteria 2024 interact with each other as indicated by double-headed arrow 2046, thereby carrying out quorum sensing.

Figure 21:
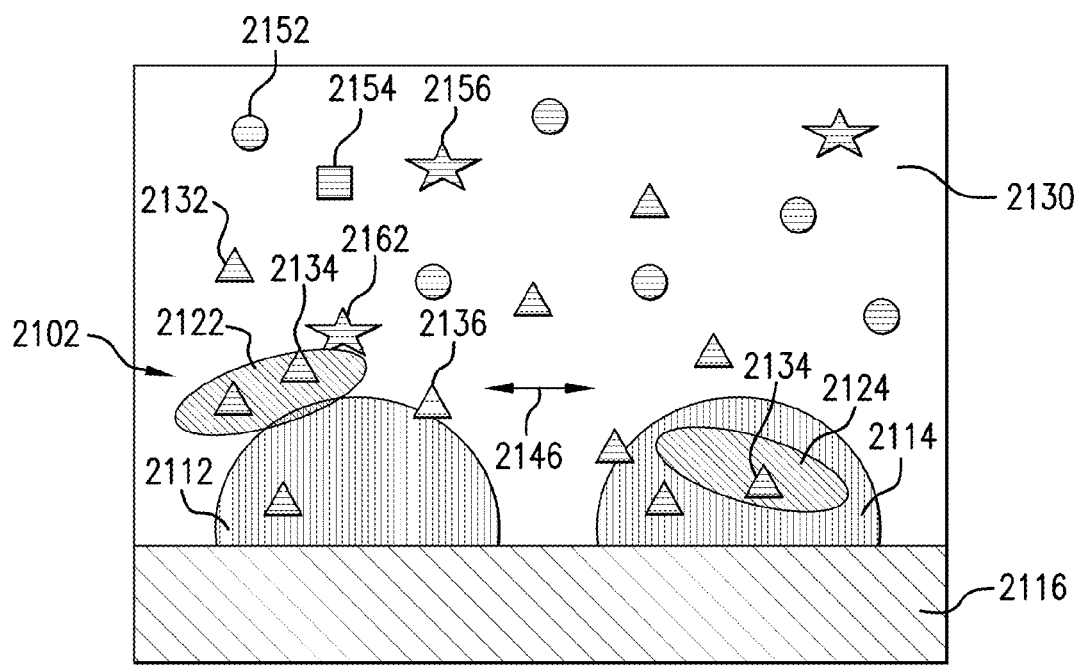
FIG. 21 is a schematic diagram showing a quorum sensor array according to one embodiment of the present invention being used to detect analytes in an aqueous solution.

By holding the bacteria in a particular pattern, i.e., the pattern of the lipid multilayer grating, the quorum sensor array of FIG. 20 has some properties similar to multi-cellular tissue with each of the bacteria acting as a "cell." Such a "synthetic cellular array" may be used to investigate the responses of multicellular tissue to various analytes as shown in FIG. 21 and described below. Although one type of array of lipid multilayer structures, i.e., lines, are shown in FIG. 20, the lipid multilayer structures of FIG. 20 may be any shape.

In one embodiment of the present invention, by detecting changes in the light scattered by the lines of the array of FIG. 20 before and after binding of the bacteria to the lipid multilayer grating, it possible to determine the affect of quorum sensing molecules on the quorum sensors of the quorum sensor array of FIG. 20. If the lipid multilayer structures and/or the bacteria bound to or encapsulated within the lipid multilayer structures are fluorescent, changes in the intensity of emitted fluorescent light may be detected before and after the binding of the bacteria to the lipid multilayer grating to determine the affect of quorum sensing molecules on the quorum sensors of the quorum sensor array of FIG. 20. Such information may be useful in providing baseline data for the array quorum sensors.

FIG. 21 shows part of a quorum sensing array 2102 according to one embodiment of the present invention used to detect analytes in a sample. Quorum sensor array 2102 comprises bacteria bound to or encapsulated within a lipid multilayer grating. The lipid multilayer grating of quorum sensor array 2102 comprises a series of lines, two of which are shown in FIG. 21, i.e., lipid multilayer line 2112 and lipid multilayer line 2114 that have been deposited on a substrate 2116 using a process such as DPN. A bacterium 2122 is bound to or encapsulated within lipid multilayer line 2112 and together form a first quorum sensor. A bacterium 2124 is bound to or encapsulated within lipid multilayer line 2114 and together form a second quorum sensor. An aqueous solution 2130 containing quorum sensing molecules 2132 (shown as triangles) surround the first and second quorum sensor. Some quorum sensing molecules 2132 are bound to or encapsulated within bacteria 2122 and 2014 as shown by reference character 2134 and some quorum sensing molecules 2132 bind to lipid multilayer lines 2112 and 2114 as indicated by reference character 2136. Bacteria 2122 and bacteria 2124 interact with each other as indicated by double-headed arrow 2046, thereby carrying out quorum sensing. The aqueous solution surrounding the quorum sensory array also includes three types of analytes, i.e., analytes 2152, 2154 and 2156. Analyte 2152 is shown binding to bacteria 2122 as indicated by reference character 2162.

In some embodiments of present invention, some quorum sensors of a quorum sensor array may comprise bacteria bound to lipid multilayer structures and some quorum sensors may comprise bacteria that are encapsulated in lipid multilayer structures.

When analytes bind or otherwise interact with the bacteria of the quorum sensor array this may have an effect on the optical properties of the quorum sensor array that may be detected by exposing the quorum sensor array to a light source and detecting the light that it scattered before and after binding. In another embodiment, the bacteria and/or the lipid multilayer grating may be florescent and the binding of an analyte to the bacteria may be detected by exposing the quorum sensors to stimulating light and detecting any change in the intensity of the fluorescent light emitted by the quorum sensor before and after binding.

In one embodiment of the present invention, a quorum sensor array may have different bacteria in different sections of the array so that the quorum sensory array may be used to detect the presence of analytes that bind to different bacteria. In one embodiment of the present invention, different receptors of bacteria may be blocked in different sections of the quorum sensor array to determine the receptor to which a particular analyte will bind.

In one embodiment of the present invention, a quorum sensor array may be used to amplify environmental signals by one lipid multilayer structure (possibly containing a bound or encapsulated living cell as part of the amplification mechanism) releasing or producing a secondary signaling molecule which diffuses to a neighboring element, which then releases the same (or another signaling molecule) thus causing a chain reaction in neighboring lipid multilayer structures. In another embodiment, a catalyst encapsulated within (or bound to) the lipid multilayers catalyzes a reaction which results in signal amplification.

The ability to control the multilayer thickness by the fabrication technique is an important attribute that determines the functionality of lipid multilayers. For example, the efficiency of optical diffraction from lipid multilayer gratings depends on the multilayer thickness, which is an important factor in their application as model cellular systems and label-free biological sensors, see Tanaka M. and Sackmann E. 2005 Nature 437 656; and Anrather D., Smetazko M, Saba M., Alguel Y. and Schalkhammer T. 2004 *J. Nanosci. Nanotechnol.* 41, the entire contents and disclosures of which are incorporated herein by reference.

Optical characterization by quantification of emitted or reflected light has been demonstrated in the context of a wide variety of fields, for example DNA and protein microarrays, chemical sensors, estimation of section thickness, 3D inspection, and measurement of critical dimensions of silicon processing. A number of calibration methods and measurement techniques have also been introduced for visual measurement systems based on optical, fluorescence, confocal and interference microscopy. In particular, approaches based on the linear relationship between fluorophore film thickness and fluorescence intensity has been successfully implemented for determination of organic residue on printed wiring boards, measurement of the thickness of photoresist films on a substrate, and use of wax films doped with rhodamine to determine film thickness by laser profilometry. Surface topography has been measured optically by immersion of the sample in a solution containing a strongly absorbing dye and measurement of transmission at the wavelength where the dye absorbs. Further examples of methods for optical characterization include the development of nanoscale markers, and fabrication of calibration standards for biological fluorescence microscopy. However, none of these prior methods of optical characterization has involved different calibration curves for measuring the height of differently shaped structures.

Quality control is a crucial step in any nanofabrication process, as is well known from the semiconductor, chemical and biomedical industries. Parallel DPN is a high-throughput nanofabrication method based on atomic force microscopy (AFM), and AFM is traditionally used for quality control of DPN-fabricated structures. AFM imaging is an established and often essential method of microstructure characterization because of its high lateral and topographical resolution, but, compared to that of optical methods, its throughput is severely limited. As a quality-control method AFM cannot keep up with the throughput of DPN fabrication. One approach to DPN uses solid, molecular inks (such as alkanethiols on gold) that form topographically smooth monolayers with sub-100 nm lateral resolution. In the case of direct deposition of biological molecules, fluid inks are typically used, especially for direct deposit of biological materials such as DNA, protein and lipids, see Lenhert S., Sun P., Wang Y. H., Fuchs H. and Mirkin C. A. 2007 Small 3 71; Demers L. M., Ginger D. S., Park S. J., Li Z., Chung S. W. and Mirkin A. 2002 Science 296 1836; Lee K B, Lim J. H. and Mirkin C. A. 2003 *J. Am. Chem. Soc.* 125 5588; and Huang L., Braunschweig A. B., Shim W., Qin L. D., Lim J. K., Hurst S. J., Huo F. W., Xue C., Jong J. W. and Mirkin C. A. 2010 Small 6 1077, the entire contents and disclosures of which are incorporated herein by reference. In the case of fluid inks, lateral resolution is often around 500 nm (with the possibility to reduce it below 100 nm when needed), yet with a level of volume control that enables single particle printing when materials are delivered in a matrix, see Bellido E., deMiguel R., Ruiz-Molina D., Lostao A. and Maspoch D. 2010 Adv. Mater. 22 352, the entire contents and disclosure of which are incorporated herein by reference. Pattern thickness is therefore an important parameter in quality control of samples fabricated by fluid DPN.

In one embodiment, the present invention provides a method for reliably measuring the heights of fluorescent multilayer features fabricated by DPN. In this method DPN is to fabricate calibration standards having arrays of fluorescent microstructures with various shapes, sizes and heights. By relating the fluorescence intensity of the fluorescent microstructures to the AFM height measurements, it is possible obtain calibration curves that can be used for high-throughput sample characterization and quantitative quality control by optical methods. These calibration curves may then be used to determine patterned microstructure height over large areas without the use of time-consuming AFM image collection. A fluorescence intensity-based structure-height quantification approach also may be useful in current and emerging nanofabrication methods such as the systematic characterization of fluorescent microstructures and nanostructures for manufacturing and the rapid screening of microstructure-function and nanostructure-function relationships.

In one embodiment, the present invention provides an optical method to reliably measure the height of fluorescent multilayers with thicknesses above 10 nm and widths above the optical diffraction limit based on calibrating the fluorescence intensity using one-time AFM height measurements. This allows large surface areas to be rapidly and quantitatively characterized using a standard fluorescence microscope. Importantly, different pattern dimensions such as 0D dots, 1D lines or 2D squares require different calibration parameters, indicating that shape influences the optical properties of the structured lipid multilayers. This method has general implications in the systematic and high-throughput optical characterization of microstructure-function and nanostructure-function relationships.

Although multilayer thickness is an important feature that determines the functionality of the lipid multilayer structures (for instance as carriers for other materials as well as optical scattering properties), reliable height characterization by AFM is slow (on the order of $\mu m^2\ min^{-1}$) and causes a bottleneck in the lithographic process. In one embodiment, the present invention provides an optical method that may be used to reliably measure the height of fluorescent multilayers with thicknesses above 10 nm and widths above the optical diffraction limit based on calibrating the fluorescence intensity using one-time AFM height measurements. This allows large surface areas to be rapidly and quantitatively characterized using a standard fluorescence microscope. Importantly, different pattern dimensions, such as 0D dots, 1D lines or 2D squares, require different calibration parameters, indicating that shape influences the optical properties of the structured lipid multilayers. This method has general implications in the systematic and high-throughput optical characterization of microstructure-function and nanostructure-function relationships.

In one embodiment, the present invention provides an approach suitable both for the fabrication of calibration standards and for high-throughput characterization of fluorescent microstructure and nanostructures created by emerging nanofabrication methods such as DPN. Image calibration and measurement of structures (especially biological structures) in the context of fluorescence microscopy are typically based on reading the intensity and location of the fluorescent structures with CCD cameras. The signal from the CCD camera is measured in terms of grey values (e.g., 0-255 for an eight-bit image), which are indications of the numbers of photons reaching the camera from the fluorophore-doped structure. Practical implementation of quantitative microscopy requires conversion of the fluorescence intensity to absolute units (e.g., the number of molecules in a particular structure) and generating calibration curves. While generating calibration curves, it is important to account for the precision of fluorescence intensity estimation and the impact of background intensity. The measurement precision (noise) of a digital microscope can be estimated from a standard slide made with uniformly fluorescent polystyrene beads or a piece of fluorescent plastic.

In one embodiment of the present invention, DPN is used to fabricate structured fluorescent standards (dots, lines, and squares of various heights). Correlations of the fluorescence intensities of the fluorescent microstructures with the feature heights measured by AFM provide a high-throughput optical quality-control approach suitable for these types of structures. An advantage of some embodiments of the method of the present invention is the elimination of the need for repetitive AFM scanning. Also, some embodiments of the present invention provide a nonintrusive approach to the use of standards that is especially suitable for soft biomolecules such as phospholipids and other similar molecules. In addition, standards of some embodiments of the present invention may be used with transparent structures of irregular shape. Some embodiments of the present invention provide the creation of custom calibration standards for a particular nanofabrication system.

In one embodiment of the present invention, a calibration standard of the present invention may be formed by depositing a patterned array of fluorescent microstructures using dip-pen lithography techniques, such as the dip-pen lithography techniques described above.

In one embodiment the calibration standard comprises a substrate and a single patterned array of fluorescent microstructures of a single shape and having different heights, although two or more fluorescent microstructures of the patterned array may have different heights.

The patterned array of fluorescent microstructures may comprise a single patterned array of fluorescent microstructures or two or more patterned arrays of microstructures. Examples of patterned array of fluorescent microstructures are a patterned array of dots, a patterned array of lines, a patterned array of squares, etc.

The fluorescent microstructures of the present invention may be made of any material or mixture of materials that is fluorescent or that may be made fluorescent using a suitable dye. In one embodiment, the fluorescent microstructures of the present invention may comprise one or more naturally fluorescent biomolecules or one or more biomolecules to which a fluorescent dye has been added. The biomolecules used in the fluorescent microstructures of the present invention may be any type of biomolecule such as a protein, a carbohydrate, a lipid, a phospholipid, a nucleic acid, etc.

Although microstructures having the shapes of dots, lines and squares are described below, the fluorescent microstructures of the present invention may have a variety of shapes.

In one embodiment, the present invention provides a calibration standard having a patterned array of quantum dots to reduce bleaching.

In one embodiment of the present invention, a calibration standard of the present invention may be used in the following manner to determine the heights of microstructures in a sample. The camera is used to detect the fluorescent intensities for a patterned array of standard fluorescent microstructures of a calibration standard. A calibration profile is then generated for the camera by hardware and/or software of the camera or from a computer, laptop computer, tablet computer, an electronic device, an electronic instrument, etc. The camera is calibrated using the calibration profile. The calibrated camera is then used to detect the fluorescent intensities of one or more fluorescent microstructures of a sample. Based on the fluorescent intensities detected by the calibrated camera, the height of each of the structures of the fluorescent microstructures on the sample may be determined.

In one embodiment of the present invention, a calibration standard of the present invention may be used in the following manner to determine the heights of microstructures in a sample. The camera is used to detect the fluorescent intensities for a patterned array of standard fluorescent microstructures of a calibration standard. A calibration profile is then generated for the camera by hardware and/or software of the camera or from a computer, laptop computer, tablet computer, an electronic device, an electronic instrument, etc. The camera is then used to detect the fluorescent intensities of one or more fluorescent microstructures of a sample. Based on the fluorescent intensities detected by the camera and the calibration profile, the height of each of the structures of the fluorescent microstructures on the sample may be determined.

For more accurate measurements, the temperature of the camera should be about the same when detecting fluorescent intensities for the fluorescent microstructures of the calibration standard and when detecting the fluorescent intensities for the fluorescent microstructures of the sample.

Although one type of fluorescent dye is described as being used to make the fluorescent lipid multilayer gratings described above and below, various types of fluorescent additives may be used to make a microstructure a fluorescent microstructure. Examples of suitable fluorescent dyes include various fluorescent organic molecules, fluorescent proteins, pigments, nanoparticles, etc.

In one embodiment, the present invention provides a method for reliably measuring the heights of iridescent multilayer features fabricated by DPN. In this method DPN is to fabricate calibration standards having arrays of iridescent microstructures with various shapes, sizes and heights. By relating the intensity of light scattered by the iridescent microstructures to the AFM height measurements, it is possible obtain calibration curves that can be used for high-throughput sample characterization and quantitative quality control by optical methods. These calibration curves may then be used to determine patterned microstructure height over large areas without the use of time-consuming AFM image collection. A structure-height quantification approach based on the intensity of light scattered by iridescent microstructures also may be useful in current and emerging nanofabrication methods such as the systematic characterization of microstructure and nanostructures for manufacturing and the rapid screening of microstructure-function and nanostructure-function relationships.

In one embodiment, the present invention provides an optical method to reliably measure the height of iridescent multilayer structures with thicknesses above 10 nm and widths above the optical diffraction limit based on calibrating the intensity of light scattered by the iridescent multilayer structure using one-time AFM height measurements. This allows large surface areas to be rapidly and quantitatively characterized. Different pattern dimensions such as 0D dots, 1D lines or 2D squares may require different calibration parameters, indicating that shape influences the optical properties of the structured lipid multilayers. In some embodiments, the method of the present invention may be employed systematic and high-throughput optical characterization of microstructure-function and nanostructure-function relationships.

Although multilayer thickness is an important feature that determines the functionality of the lipid multilayer structures (for instance as carriers for other materials as well as optical scattering properties), reliable height characterization by AFM is slow (on the order of $\mu m^2 \, min^{-1}$) and causes a bottleneck in the lithographic process. In one embodiment, the present invention provides an optical method that may be used to reliably measure the height of iridescent multilayers with thicknesses above 10 nm and widths above the optical diffraction limit based on calibrating the intensity of light scattered by the iridescent multilayer structure using one-time AFM height measurements. This allows large surface areas to be rapidly and quantitatively characterized. Importantly, different pattern dimensions, such as 0D dots, 1D lines or 2D squares, require different calibration parameters, indicating that shape influences the optical properties of the structured lipid multilayers. This method has general implications in the systematic and high-throughput optical characterization of microstructure-function and nanostructure-function relationships.

In one embodiment, the present invention provides an approach suitable both for the fabrication of calibration standards and for high-throughput characterization of iridescent microstructure and nanostructures created by emerging nanofabrication methods such as DPN. Image calibration and measurement of iridescent structures is carried using optical microscopy where the iridescent structures are illuminated at various angles, and the intensity and location of the light scattered from the iridescent structures is imaged with a CCD camera. The signal from the CCD camera is measured in terms of grey values (e.g., 0-255 for an eight-bit image), which are indications of the numbers of photons reaching the camera from the iridescent structure. Practical implementation of quantitative microscopy requires conversion of the iridescence intensity to absolute units (e.g., the number of molecules in a particular structure) and generating calibration curves. While generating calibration curves, it is important to account for the precision of iridescence intensity estimation and the impact of background intensity, as well as the illumination conditions (especially angle, distance from the sample, and intensity). The measurement precision (noise) of a digital microscope can be estimated from a standard iridescent sample, such as a silicon diffraction grating.

In one embodiment of the present invention, DPN is used to fabricate structured iridescent standards (dots, lines, and squares of various heights). Correlations of the intensities of scattered light from of iridescent microstructures with the feature heights measured by AFM provide a high-throughput optical quality-control approach suitable for these types of structures. An advantage of some embodiments of the method of the present invention is the elimination of the need for repetitive AFM scanning. Also, some embodiments of the present invention provide a nonintrusive approach to the use of standards that is especially suitable for soft biomolecules such as phospholipids and other similar molecules. In addition, standards of some embodiments of the present invention may be used with transparent structures of irregular shape. Some embodiments of the present invention provide the creation of custom calibration standards for a particular nanofabrication system.

In one embodiment of the present invention, a calibration standard of the present invention may be formed by depositing a patterned array of iridescent microstructures using dip-pen lithography techniques, such as the dip-pen lithography techniques described above.

In one embodiment the calibration standard comprises a substrate and a single patterned array of iridescent microstructures of a single shape and having different heights, although two or more iridescent microstructures of the patterned array may have different heights.

The patterned array of iridescent microstructures may comprise a single patterned array of iridescent microstructures or two or more patterned arrays of microstructures. Examples of patterned array of iridescent microstructures are a patterned array of dots, a patterned array of lines, a patterned array of squares, etc.

The iridescent microstructures of the present invention may be made of any material or mixture of materials that is iridescent. The biomolecules used in the iridescent microstructures of the present invention may be any type of biomolecule such as a protein, a carbohydrate, a lipid, a phospholipid, a nucleic acid, etc.

The iridescent microstructures of the present invention may have any shape including dots, lines, squares, circles, rectangles, triangles, etc.

In one embodiment of the present invention, a calibration standard of the present invention may be used in the following manner to determine the heights of microstructures in a sample. The camera is used to detect the light intensities for light scattered by a patterned array of standard iridescent microstructures of a calibration standard. A calibration profile is then generated for the camera by hardware and/or software of the camera or from a computer, laptop computer, tablet computer, an electronic device, an electronic instrument, etc. The camera is calibrated using the calibration profile. The calibrated camera is then used to detect the intensities of light scattered by one or more iridescent microstructures of a sample. Based on the intensities of scattered light detected by the calibrated camera, the height of each of the structures of the iridescent microstructures on the sample may be determined.

In one embodiment of the present invention, a calibration standard of the present invention may be used in the following manner to determine the heights of microstructures in a sample. The camera is used detect the light intensities for light scattered by a patterned array of standard iridescent microstructures of a calibration standard. A calibration profile is then generated for the camera by hardware and/or software of the camera or from a computer, laptop computer, tablet computer, an electronic device, an electronic instrument, etc. The camera is then used to detect the intensities of light scattered by one or more iridescent microstructures of a sample. Based on the fluorescent intensities detected by the camera and the calibration profile, the height of each of the structures of the fluorescent microstructures on the sample may be determined.

For more accurate measurements, the temperature of the camera should be about the same when detecting fluorescent intensities for the fluorescent microstructures of the calibration standard and when detecting the fluorescent intensities for the fluorescent microstructures of the sample.

The substrate of various embodiments of the present invention may be virtually any type of substrate on which lipid multilayer gratings may be deposited or grown such as glass, plastic, paper, a semiconductor material, etc.

EXAMPLES

Example 1

Methods. DPN patterning. A commercial dip-pen nanolithography (DPN) instrument equipped with an environmental chamber (NScriptor, NanoInk) was used with a one-dimensional tip array with 26 tips (Type F, A26). Optical alignment procedures were used to align the gratings on prefabricated waveguides. Ink preparation (including the use of fluorescently labeled, biotinylated and metal chelating lipids) was carried out as described elsewhere. The tips were dipped in the inkwells for up to 30 minutes at 23° C. and 70% relative humidity. The gratings were written on PMMA sheets (HESA®Glas HT, Notz Plastics) and treated with isopropanol and ultrapure (Satorius) water (5 minutes sonication both). For total internal reflection fluorescence (TIRF) imaging, PMMA (107 kD, PSS Mainz) was spin-coated from a 15% toluene solution onto glass coverslips to a thickness of 90 nm. The writing process took place at 45% relative humidity and at tip velocities of ranging from 0.1 to 10 µm/s. Substrates before use and the samples after production were stored in a nitrogen atmosphere or vacuum, which minimized hydration-induced spreading.

Grating characterization. Atomic force microscopy measurements were done with a Dimension 3100 (Veeco) in a clean room. Microscopic diffraction images were taken by an inverted TE 2000 fluorescence microscope (Nikon) with a 6× objective and a color camera (Nikon Digital Sight). The gratings were illuminated in transmission through the PMMA substrate by a 150-W halogen cold light source (Schott KL 1500 LCD) at an angle of ca. 70° to the surface normal perpendicular to the grids. Color spectra were measured with a DC 480 microscope (Leica) with a 10× objective connected to a spectrometer (NanoCalc 2000) and a halogen light source (DH-2000 FHS, Mikropack) through four optical fibers in one wire. Fibers 1 and 2 led to the halogen lamp, which illuminated two 40-µm-diameter spots on the surface for orientation purposes; fibers 3 and 4 led to the spectrometers. A 3-mm-wide slot in the optical light path between the objective and the eye piece functioned as a monochromator. TIRF micrographs were taken by the inverted TE 2000 fluorescence microscope (Nikon) with a 100× objective, the W-TIRF illuminator (Nikon), T-PFS perfect focus unit (Nikon), and a CCD camera (Hamamatsu Orca-ER).

Waveguide coupling. A single-mode optical strip waveguide of 8-µm width was obtained by exposure of PMMA to DUV radiation through a quartz-chromium mask. Although the guiding is relatively weak because the low refractive index contrast (ca. 0.005) between that of the exposed surface and the substrate (refractive index of 1.48) 3, this method offers a cost-efficient way to fabricate optical waveguides for visible wavelengths. The substrate was 1 mm thick. A mask aligner (EVG 620) operating at a wavelength of) λDUV=240-250 nm was used applying an exposure dose of 2 J/cm². A bake at 70° C. for 4 hours after the DUV exposure expelled volatile degradation products and durable radicals from the waveguide.

Protein detection. Protein-sensing experiments were carried out under liquid conditions on an inverted microscope, and time-lapse diffraction images were taken as described above. A homemade rectangular polydimethylsiloxane (PDMS) barrier was placed around the grating and filled with 200 µl of a buffer solution (PBS) containing 0.5% BSA and allowed to incubate for 10 minutes before addition of the streptavidin solution. Unless otherwise noted, the streptavidin solution was added by replacement of half (100 µl) of the solution from the fluid cell with a protein solution of twice the target concentration. Optical noise from sources such as reflection from the fluid cell and air-water interface, solvent evaporation, thermal drift, and general background light was cancelled by division of the signal from the target binding gratings by the signal from pure 1,2-dioleoyl-sn-glycero-3-phosphocholine (DOPC) control grating monitored in parallel on the same surface unless otherwise noted. In order to ensure reproducible immersion of the lipid gratings in solution without induction of structural changes, the solution was added within a glove box in a nitrogen atmosphere, where the lyotropic lipid multilayers are "frozen" by dehydration. Further stability upon immersion was ensured by addition of the 0.5% BSA blocking agent to the solution. BSA prevents spreading of lipid multilayers by binding to the substrate on which the lipid multilayers are deposited. The data were analyzed with ImageJ (v 1.38x) and Origin 6.1 by measurement of the intensity of light measured from a grating and subtraction of the background intensity from it.

Results. The tendency for fluid lipid multilayers to spread under solution, as well as to be disrupted upon crossing the air-water interface, poses a challenge for immersion. It was found that the DOPC-based gratings could be immersed and remain stable under water for at least several days when patterned on hydrophobic PMMA surfaces and when the gratings were immersed in solution containing 0.5% BSA at humidity well below 40% (e.g., in a nitrogen atmosphere). The reason for immersion at low humidity is to freeze the lipids effectively into place so that they are not disrupted by the air-water interface. Further, the 0.5% BSA blocking agent can be expected to block the background surface and slow the spreading. As the difference between spreading behaviors in humid air and under water on hydrophobic surfaces involves different interfacial energies, spreading can be expected to proceed by different mechanisms, i.e., monolayer and bilayer spreading, the kinetics of which have been quantitatively described as a balance between the spreading force and the resistive drag. In contrast to an observable change in contact angle typical for spreading of bulk sessile droplets, lipid multilayers tend to spread as molecularly thin and homogeneous layers. The hydrophobic chain is well known, e.g., from Langmuir-Blodgett films of amphiphilic molecules, to tend to orient toward the air at the air-water interface as well after transfer onto hydrophilic surfaces. Furthermore, evidence has been published that monolayers spread on hydrophobic surfaces under water. The readier spread of lipids in humid air than under water under the conditions described in this example may be attributed to the difference between these preferred spreading mechanisms and the friction within these molecularly thin precursor films, as well as to surface passivation by the BSA blocking agent.

Example 2

Materials and Procedures. 1,2-dioleoyl-sn-glycero-3-phosphocholine (DOPC, 20 g $L^{-1}$ solution in chloroform) and 1,2-dioleoyl-sn-glycero-3-phosphoethanolamine-N-lissamine rhodamine B sulfonyl (DOPERB, 1 g $L^{-1}$ solution in chloroform) from Avanti Polar Lipids, Inc. (Alabaster, Ala.), and used as received. Rhodamine B (RB) is an orange dye with an excitation wavelength of 557 nm and an emission of 571 nm that is imaged with a Nikon G-2E/C filter set. It is known to produce a fluorescent field of reproducible intensity with a good resistance to photo-bleaching at low excitation power. A 1 mol % solution of DOPE-RB is prepared in DOPC, and the mixture is pipetted into an inkwell delivery system made by NanoInk, Inc. (Skokie, Ill.), for tip inking. This ink formulation is used throughout the study reported here unless stated otherwise. The inkwell is kept under vacuum overnight so that the chloroform would evaporate. The inks are kept in closed tins to prevent their exposure to external light sources. F- and M-type 1D cantilever arrays (NanoInk, Inc.) are used for DPN. These arrays ware dipped into the inkwell microchannels for 5 minutes to coat the tip with DOPC ink. Glass slides (No. 48366-227 from VWR (West Chester, Pa.)) and oxygen plasma cleaned for 2 minutes at low power just before DPN. All experiments are performed at ambient relative humidity (53±3%) and temperature (25±2° C.). A Ti-E epifluorescence inverted microscope (Nikon Instruments, Inc., Melville, N.Y.) fitted with a Retiga SRV (QImaging, Canada) CCD camera (1.4 megapixel, Peltier cooled to −45° C.) is used to image the fluorescent patterns created. All images for generation of intensity-by-height calibration curves are captured at the lowest gain setting with no binning with a Nikon 10× objective lens (645 nm/pixel, numerical aperture (NA)=0.3) with different exposure times. These images are then saved in their native 16-bit tiff black-and-white format and analyzed with ImageJ software. In ImageJ, the images were converted to eight-bit format, 256 grey values (the brightest, saturated regions had the maximum intensity of 255 grey values). The images with different exposure times are merged into a stack of images with different exposure times (0.2 ms-8 s). For measurement of fluorescence intensity of the dot features, a region of interest (ROI) is drawn around the dot in ImageJ, and the intensity of the brightest pixel in the dot is measured and analyzed with the 'plot Z axis profile' function in the stacks menu of ImageJ. For line features, rectangular ROIs (one pixel wide) were drawn perpendicular to the line, and the maximum intensity of the line cross section is measured as described for the dot measurements above. Three cross sections are measured per line, and the average of the three cross-section maxima are taken as the intensity for the line. In the case of square features, square ROIs were drawn just inside the perimeter of the patterned square feature, and an average is taken over the ROI area. As the exposure times decrease, the images become less bright and eventually disappeared into the background, as expected. After fluorescence microscope imaging, the patterns were imaged with a Dimension 3000 AFM (Veeco Instruments Inc., Plainview, N.Y.) using alternate contact mode cantilevers (No. OMCL-AC160TS-W2), 7 nm nominal tip radius, 15 μm tip height, 42 N $m^{-1}$ spring constant, (Olympus, Center Valley, Pa.). Feature heights are measured by AFM according to the same approach as taken for measurement of dot, line and square feature heights during intensity measurements as described above. The AFM height is then compared to the height estimated from fluorescence intensity calibration curves.

Figure 22:
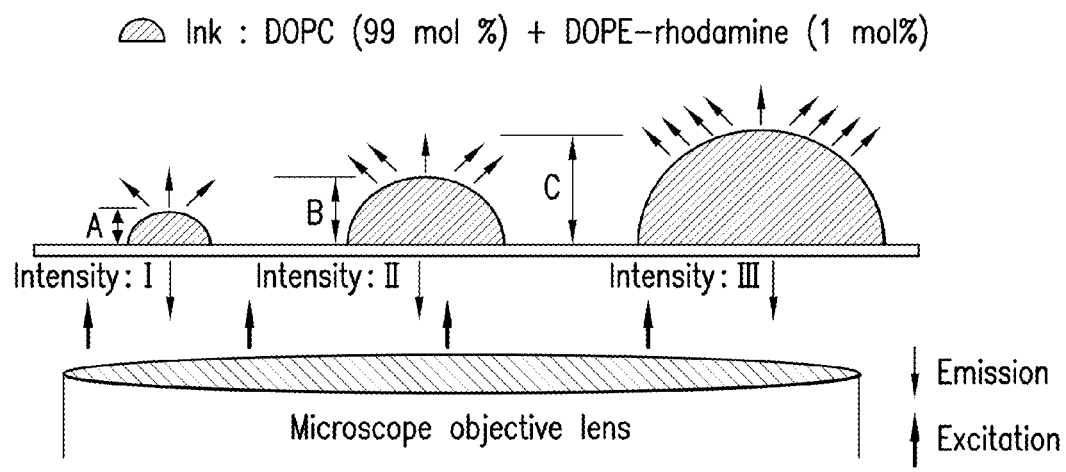
FIG. 22 shows fluorescent microstructures being excited using light transmitted through a microscope objective lens and the fluorescent microstructures emitting light in response according to one embodiment of the present invention.
Figure 23:
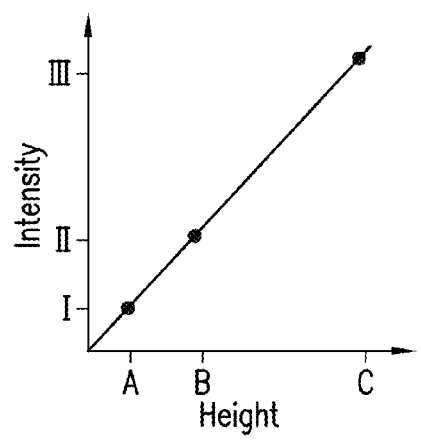
FIG. 23 is a graph of emitted light intensity vs. height for three hypothetical fluorescent microstructure dots according to one embodiment of the present invention.
Figure 24:
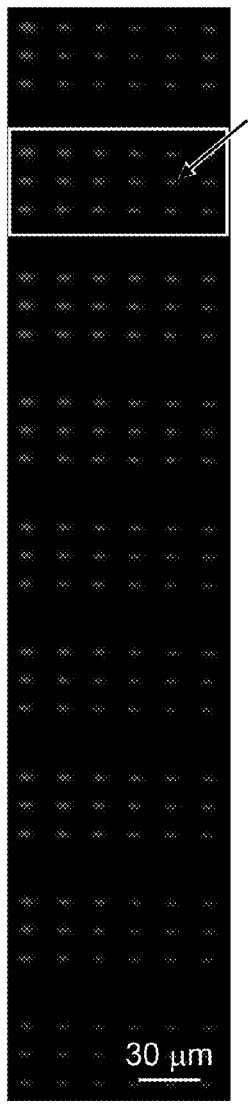
FIG. 24 is a fluorescent microscopy image of 6×3 DOPC dot arrays (15 µm pitch) created with M-type cantilevers.

Results. FIGS. 16, 22 and 23 show a schematic diagram of the overall process of measuring the intensity of fluorescent lipid microstructures for determination of their height by fluorescence intensity using height calibration curves. FIG. 16 shows the chemical structures of the lipid molecules used to fabricate the calibration standards used in this example. In the first step, 1,2-dioleoyl-sn-glycero-3-phosphocholine (DOPC) is doped with 1 mol % red dye 1,2-dioleoyl-sn-glycero-3-phosphoethanolamine-N-(lissamine rhodamine B sulfonyl) (DOPE-RB) and patterned on a glass slide. Sequential images of the fluorescent lipid patterns were recorded, and the intensities (grey values, 0-255) of the features in each image (corresponding to each exposure time) are proportional to the feature height. As illustrated in FIG. 22, taller patterns have higher fluorescent intensity (I<II<III), as shown by the number of arrows over each feature, and appear brighter in the fluorescence image as shown with the three hypothetical dots of different heights (a<b<c). The intensity of each structure is measured after DPN with ImageJ software with intensity values ranging from 0 to 255 (for an eight-bit image). FIG. 23 shows the expected relationship between the feature height and the fluorescence intensity registered, with taller dots showing higher intensities.

Thus a calibration curve for the features can be drawn using the slope of FIG. 23. This results in a calibration curve of sensitivity (grey values/s) vs. the feature height. By measuring the feature intensity at a certain exposure time, it is possible to estimate the height of the fluorescent feature using the calibration curve. This allows rapid quality control of the patterned features, modification of the DPN parameters (if need be) and enables tunable control over the height of lipid microstructures.

In order to demonstrate the relationship between feature height and recorded intensity, features in different shapes, i.e., dots, lines and squares, are created. For dots, a pattern of 6×3 (15 μm pitch) dots with DOPC created using DPN with M-type cantilevers is shown in FIGS. 24, 25, 26 and 27. FIG.

Figure 25:
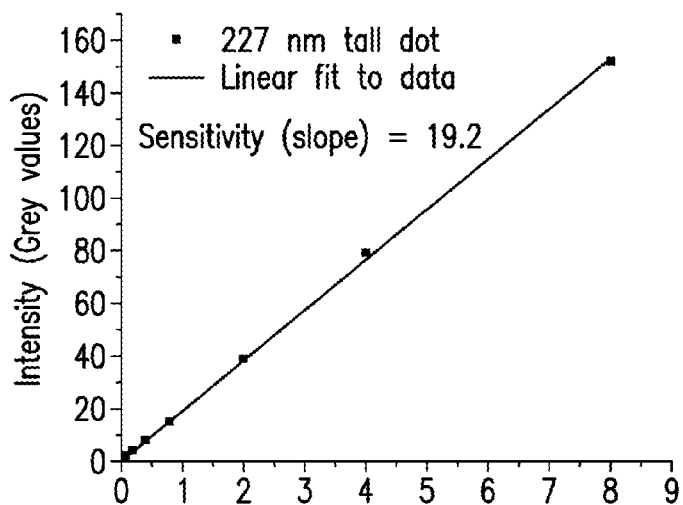
FIG. 25 is a graph of emitted light intensity vs. exposure time curve for a 227 nm tall dot indicated by an arrow on FIG. 24.
Figure 27:
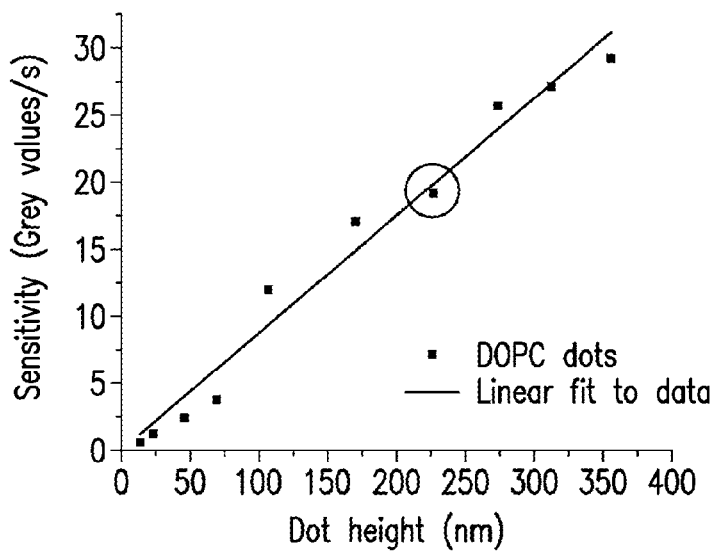
FIG. 27 is a sensitivity vs. dot height calibration curve for all the dot heights measured in the white rectangle of FIG. 24 with each of the data points in this figure being obtained by plotting the slope vs. the height measured with AFM.
Figure 26:
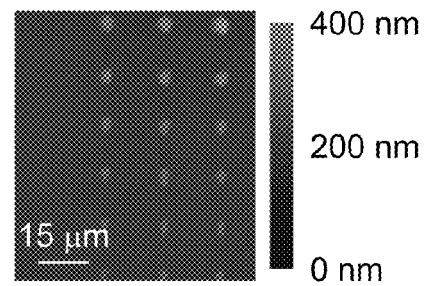
FIG. 26 is an atomic force microscopy (AFM) height image of one of the dot arrays (dot radii 640 nm to 2.5 µm) enclosed in a white rectangle of FIG. 24 and having dot heights ranging from 14 to 356 nm.

24 is the fluorescent micrograph of the dots. Dot intensities are measured as that of the brightest pixel in the dot. The dots are of different intensities indicating a difference in height. FIG. 25 is an intensity vs. exposure time curve for a 227 nm tall dot, indicated by an arrow in FIG. 24, obtained by measuring the fluorescent intensity of that dot using ImageJ over the various exposure times. FIG. 26 is an AFM height image of one of the dot arrays (dot radii 640 nm to 2.5 µm) enclosed in a white rectangle in FIG. 24 having dot heights ranging from 14 to 356 nm. FIG. 27 is a sensitivity (grey values/s) vs. a dot height calibration curve for all the dot heights measured. Each of the data points in FIG. 27 is obtained by plotting the slope vs. the height measured with AFM. FIG. 27 shows the calibration curve obtained (grey values/s vs. dot height) using the intensity measurement over various exposure times. FIG. 27 also shows that higher features exhibit higher values of sensitivity (grey values/s) and need lower exposure times to reach the saturated intensity grey value (255).

Figure 28:
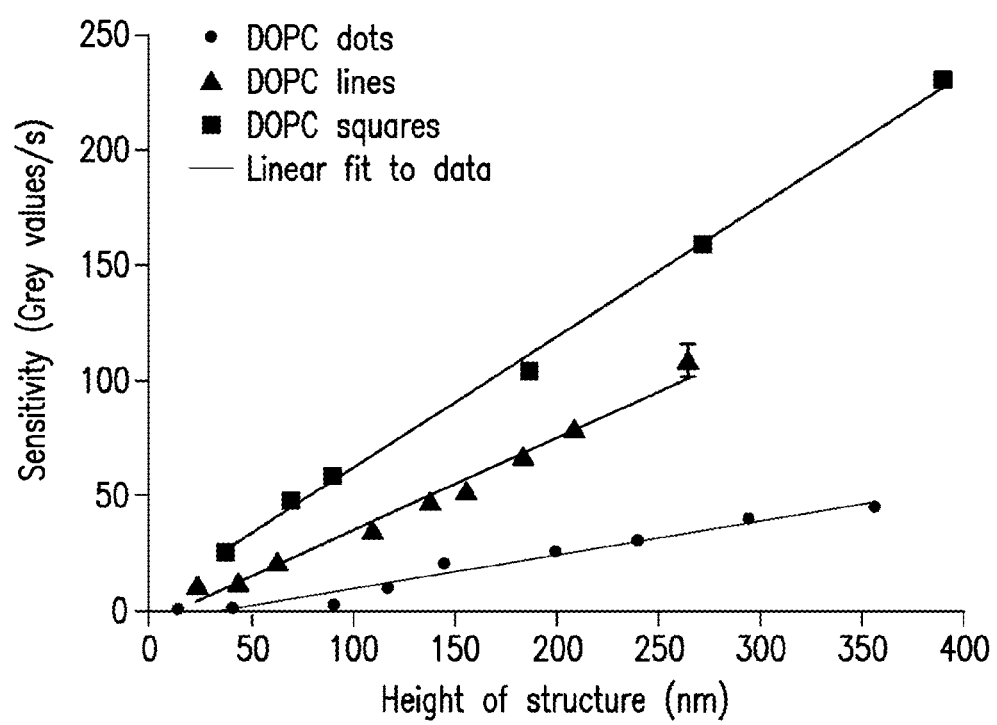
FIG. 28 is a plot of calibration curves obtained for three feature shapes: dots, lines and squares of an array of fluorescent microstructures according to one embodiment of the present invention.

How shape of the fluorescent microstructure affects the recorded intensity is also determined In addition to arrays of dots, arrays of line-shaped fluorescent microstructures and arrays of square-shaped microstructures are created and the sensitivity vs. feature height calibration curves are obtained as shown in FIG. 28. The highest height obtained for dots is ~350 nm while the highest height for lines and squares is ~300 nm and ~400 nm, respectively. However, the trend of lower features exhibiting lower intensity values is observed for all the three shapes. The three shapes have significantly different slopes: 0.087 for dots, 0.337 for lines and 0.587 grey values/s/nm for square patterns. The number of bright rhodamine dye molecules enclosed in the three shapes is different and this directly affects the sensitivity of measurement based on structure height.

Figure 29:
FIG. 29 is a fluorescent microscope image of a large area (0.12 mm$^2$) FSU pattern created by moving the DOPC-coated tip at a tip speed of 75 nm/s.
Figure 30:
FIG. 30 is a close-up image of the one of the FSU letters enclosed by the white square in FIG. 29.
Figure 31:
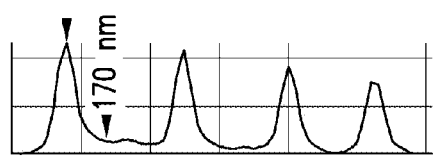
FIG. 31 is an intensity profile of the FSU letters at the region of the white line, registering a value of 115 which is equivalent to a height of 170 nm.

In order to test this approach of quantifying the feature height by using the florescence intensity of lipid features, the fluorescence intensity is used to measure the height of a "FSU" pattern created with lines as shown in FIGS. 29, 30, 31, 32 and 33. The calibration curve used to measure the height of the FSU letters is the calibration curve obtained for the line patterns in FIG. 28, i.e., slope of 0.337 grey values/s/nm. The FSU pattern is created and imaged under the fluorescent microscope using the 10× objective lens over different exposure times (800 µs-8 s), and its height is immediately measured with tapping mode AFM. FIG. 29 is a fluorescent microscope image of a large area (0.12 mm²) FSU pattern created by moving the DOPC-coated tip at a tip speed of 75 nm/s. FIG. 30 shows a close-up fluorescent microscope image of the FSU pattern imaged at 2 s exposure time. The height of the same "F" letter measured across the region denoted by the white line in FIG. 30 using the calibration curve of FIG. 31, is estimated to be ~170 nm using Equation 1 below:

$$\text{Height (nm)} = \frac{\text{Measured intensity from fluorescence image(grey values)}}{\text{Slope of the line calibration curve (grey values/s/nm)} * \text{Exposure time(s)}} = \frac{115}{0.337 * 2} = 170 \quad (1)$$

Figure 32:
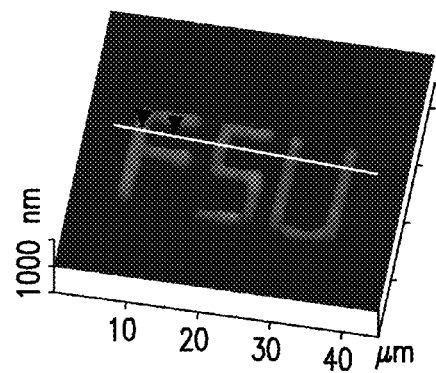
FIG. 32 is an AFM height image of the same FSU logo of FIG. 30 with a measurement performed at the same location of the white line as shown in FIG. 30.
Figure 33:
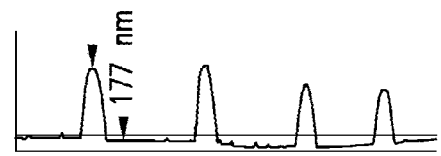
FIG. 33 is a height trace showing a value of 177 nm for the letter "F" of FIG. 32.

FIG. 32 is AFM height image of the same FSU logo of FIG. 30 at the same exposure time, i.e., 2 s, with a measurement performed at the same location of the white line as shown in FIG. 30. The height is measured to be 177 nm as shown in FIG. 33. The error between the estimated feature height obtained using Equation 1 and the measured height is within an error of ~4%.

The actual feature heights of ten different measurements measured by AFM are compared to those estimated using the fluorescence intensity of the structures, and the differences are found to be within an average of 7%±4% of the feature heights measured with AFM. Further, the lowest height of the fluorescent microstructure that could be reproducibly quantified by this approach is ~10 nm, which is the equivalent of three DOPC lipid bilayers (which are 3.5 nm).

This close matching of the estimated feature height (from calibration curves obtained using fluorescence intensity measurements) to the actual feature height obtained using AFM measurements in a different experiment validates this approach of using optical quality control to determine feature height. This control over height may be important in developing novel applications of lipid microstructures as diffraction gratings. Further, this nonintrusive optical approach may be extended to systems where the lipid microstructures can be envisioned to act as carriers of other biomaterials essential to understanding cell-structure relationships. With the base lipid feature height vs. intensity calibrated, it may be possible to estimate the amount of biomaterial carried with the lipid microstructure. This approach may also be used with other similar liquid (lyotropic) biocompatible ink systems using optical quality control as the height-determining method. Optical quality can be especially useful for large-area feature height determination where slow AFM scanning is not desirable.

Figure 34:
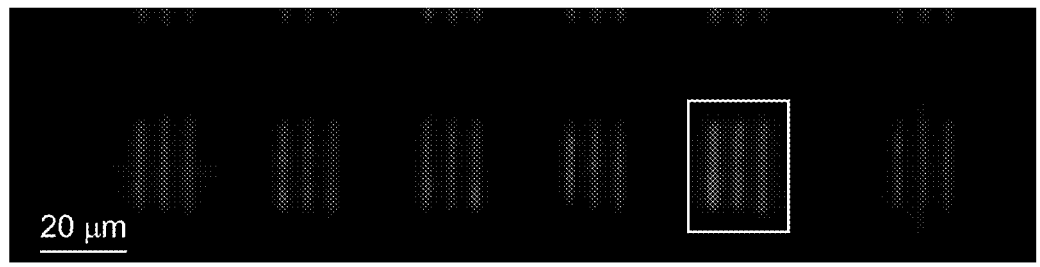
FIG. 34 is a fluorescent micrograph of line patterns drawn with doped DOPC ink by moving the tip at a speed of 100 nm/s with the lines being 20 µm long.
Figure 35:
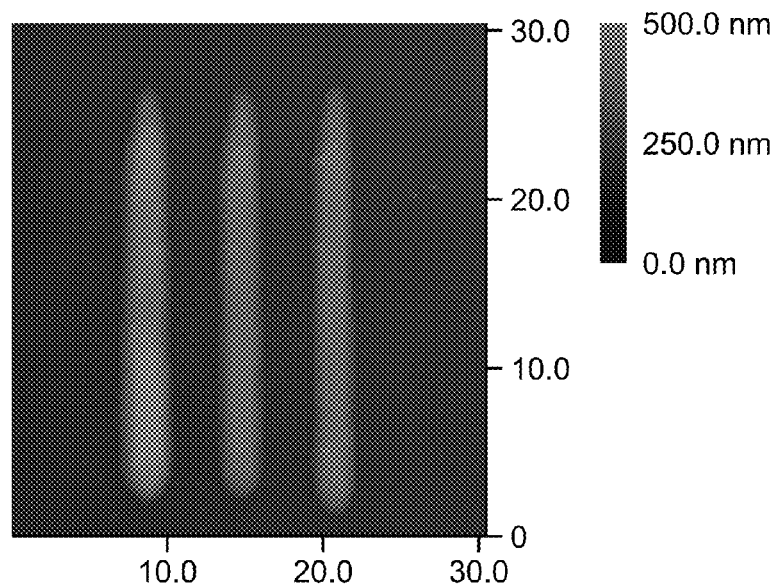
FIG. 35 is an AFM height image of the lines enclosed by the white square in FIG. 34, imaged in alternate contact mode.
Figure 36:
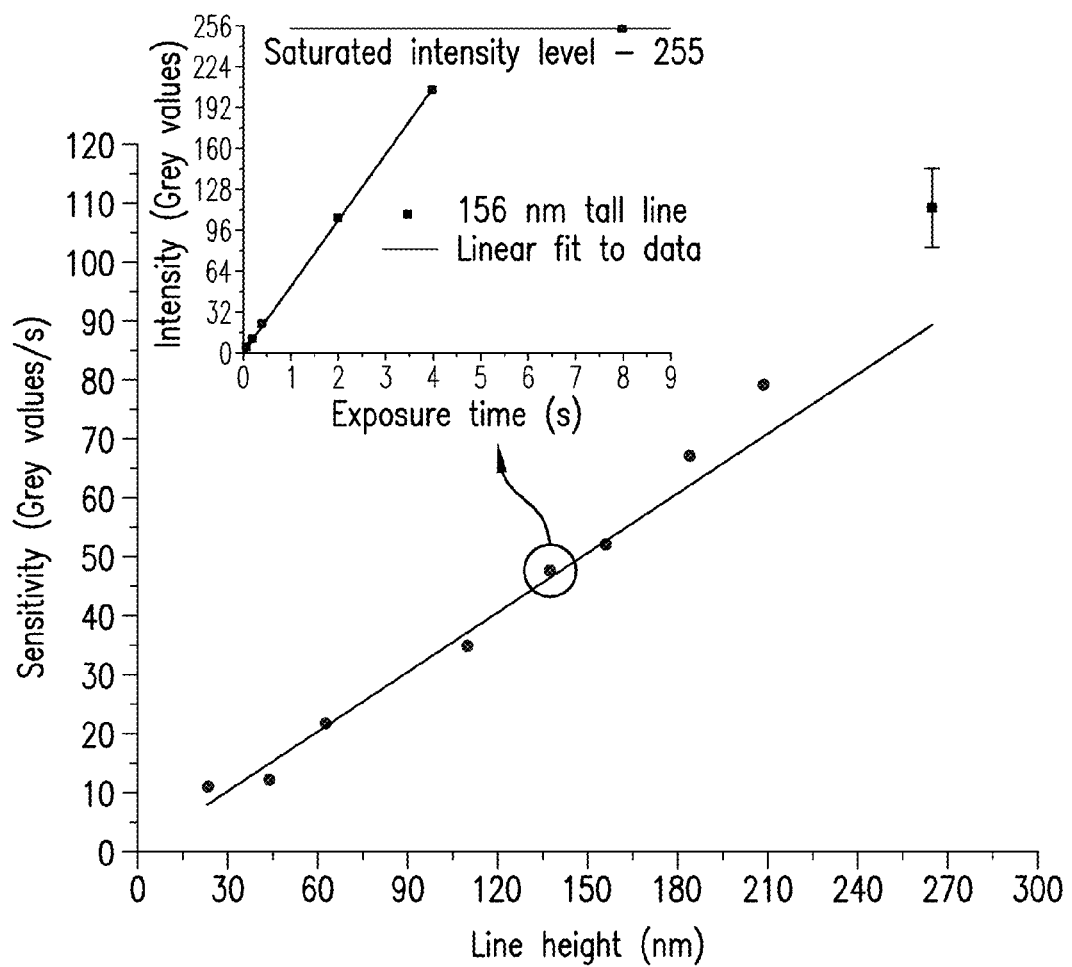
FIG. 36 is a graph of sensitivity vs. a line height calibration curve obtained using the slope (grey values/s) of each line height with an inset graph showing a typical linear relationship observed between the exposure time (s=seconds) and intensity (grey values) registered for a 156 nm tall line.

A pattern of DOPC line patterns created by parallel DPN (with each tip drawing an array of three parallel lines) is shown in FIGS. 34, 35 and 36. FIG. 34 is a fluorescent micrograph of line patterns drawn with doped DOPC ink, by moving the tip at a speed of 100 nm/s with the lines being 20 µm long. The average width of the lines is ~300 nm.

FIG. 34 is a fluorescence micrograph of the lines taken through a 10× objective lens. FIG. 35 shows the AFM height image of one representative line array. The average height of the lines is measured to be 304, 213 and 215 nm (left to right). FIG. 36 is a graph of sensitivity vs. a line height calibration curve obtained using the slope (grey values/s) of each line height with an inset graph showing a typical linear relationship observed between the exposure time (s) and intensity (grey values) registered for a 156 nm tall line. The saturated intensity level (255) is also shown as a horizontal line. Average width of the lines is ~2.7 µm.

For purposes this example, the intensity of a feature is defined by the maximum intensity of a pixel within that feature; line fluorescence intensities were defined as that of the brightest pixel in a cross section of the line. Because different line heights require different exposure times to be within the dynamic range of the camera (so that large features would not be saturated while others were not visible), the same area is systematically imaged using different exposure times and plotted as the intensity against exposure time. FIG. 36 (inset) shows such a plot for a 156 nm high line and indicates a linear dependence of line heights on fluorescence intensity measured over the exposure times. The slope of the relation between measured intensity and exposure time may be referred to as the "sensitivity" of each feature, and it has units of grey values $s^{-1}$. For example, the resulting sensitivity for a 156 nm tall line is 52 grey values $s^{-1}$ and is plotted as an inset in FIG. 36. A series of these fluorescence sensitivity and AFM height measurements for all the different line heights resulted in a calibration curve (sensitivity against height) as shown in FIG. 36, and a linear dependence is observed.

Figure 37:
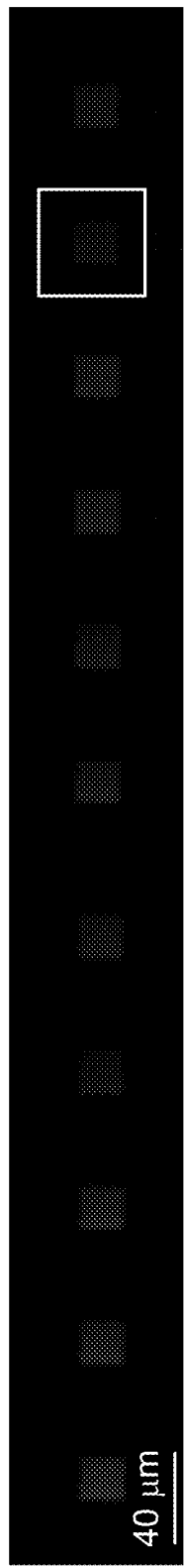
FIG. 37 is a fluorescent micrograph of square patterns drawn with doped DOPC ink.

FIG. 37 is a fluorescent micrograph of square patterns drawn with doped DOPC ink.

Figure 38:
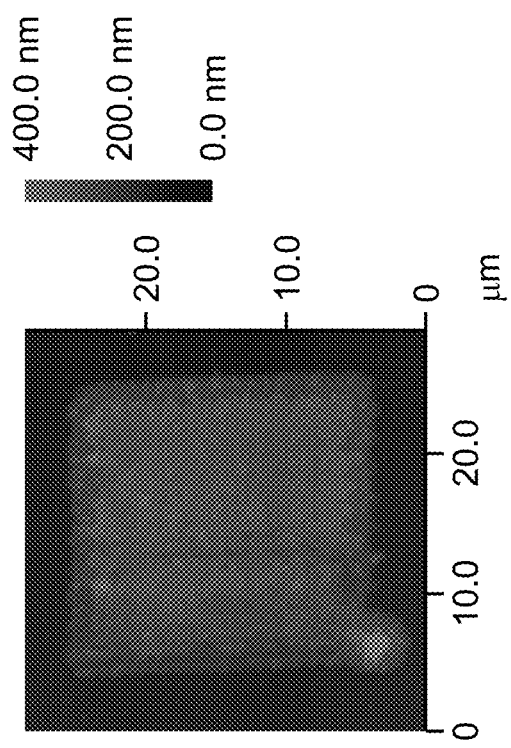
FIG. 38 is an AFM height image of the square enclosed by the white square in FIG. 37 imaged in alternate contact mode.

FIG. 38 is an AFM height image of the square enclosed by the white square in FIG. 37, imaged in alternate contact mode.

Figure 39:
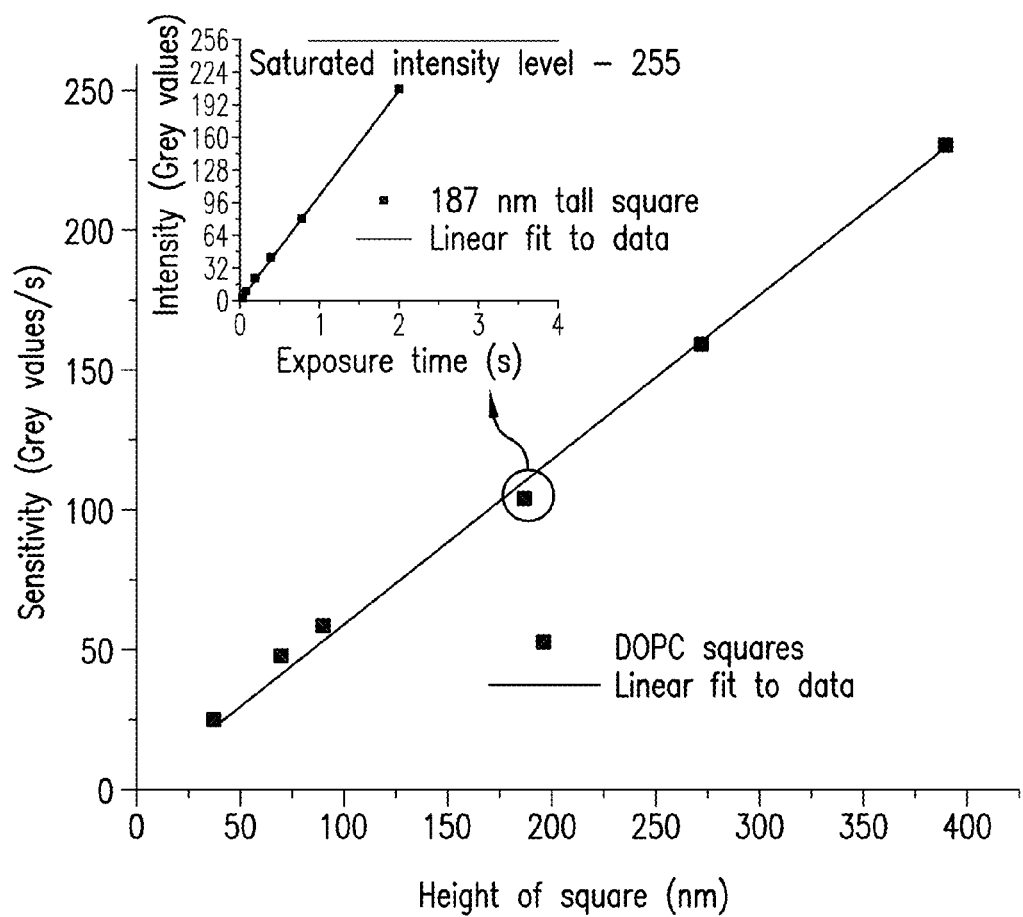
FIG. 39 is a graph of sensitivity vs. line height calibration curve obtained using the slope (grey values/s) of each line height with an inset graph showing a typical linear relationship observed between the exposure time (s) and intensity (grey values) registered for a 187 nm tall square.

FIG. 39 is a graph of sensitivity vs. line height calibration curve obtained using the slope (grey values/s) of each line height with an inset graph showing a typical linear relationship observed between the exposure time (s) and intensity (grey values) registered for a 187 nm tall square. Square intensities are defined as the average intensity of the flat region within the square. The saturated intensity level (255) is shown as a horizontal line.

As discussed above, although a reliable linear trend is observed in which taller features showed higher intensities for all three shapes, the different structure geometries had significantly different slopes: $0.087 \pm 0.003$ grey values $s^{-1}$ $nm^{-1}$ for dots, $0.337 \pm 0.012$ for lines, and $0.587 \pm 0.009$ for squares, as shown in FIG. 28. A possible explanation is a proximity effect, i.e., that light emitted from a single pixel-sized cross section of the surface is picked up by more than one pixel, thus leading to extra illumination per pixel for higher-dimensional structures, which would be described by the point spread function for the optical system being used. In order to estimate the lateral resolution of a fluorescence microscope, the Rayleigh criterion is typically used ($d=0.61\lambda/NA$, where d is the separation distance between emitters, $\lambda$ is the wavelength of emitted light, and NA is the numerical aperture). In the case of the calibration shown in FIG. 28, with our 10× objective, there is a d of 1.16 µm, and therefore a rather large surface area is imaged by each pixel.

The use of higher NA optics may reduce this effect and provide insights into how sub-wavelength structures influence optical properties. As the aspect ratio of features can affect calibration, it is worth noting that aspect ratios (heights/widths) in constructive lithographic methods are typically low, and in the case of lipid DPN, typically less than 0.1.

There also may be further structure-dependent effects. For example, one possibility is that the dye molecules have a preferred orientation within the liquid crystalline lipid structures that affects their optical cross sections and therefore absorption efficiencies. The difference in calibration responses for dots, lines and squares with these inks indicates that a reliable calibration will require use of a standard sample with the same types of structures as those to be fabricated. Worth noting is that all the linear fits go roughly through the origin; i.e., sensitivity is zero for a structure of height zero, so signal to background noise selectivity is good.

To test further the reliability of this characterization method, the curve of emission intensity plotted against dye concentration is investigated as a control. The intensity is found to increase linearly with dye concentration (0.125-2 mol %) for the same feature height. Because different objective lenses, with different NA, will collect different amounts of light, different objectives are calibrated by using the same lens to measure a set of dots of the same height using 4×, 10×, and 40× magnification lenses. As expected, the higher-magnification (and higher-numerical-aperture) lens collected more light per pixel and correspondingly exhibited higher calibration curves, i.e., steeper slope of the intensity plotted against exposure time.

Therefore, DPN may be used to produce calibration standards for optical microscopy and these same standards may be used for the high-throughput determination of feature heights of lipid microstructures and nanostructures using a standard fluorescence microscope. Higher features correspond to greater intensity (grey values) registration, and this linear relationship can be used to determine the feature heights of subsequent patterns written with the same ink. This rapid height characterization method is not limited to DPN; any other micro/nano-patterning technique like micro-contact printing may also be used to create the fluorescent structures.

The optical response depends on the shape of the fluorescent microstructures such as dots, lines or squares. The rapid nonintrusive optical calibration and height estimation approach of some embodiments of the present invention may be used with systems in which the lipid microstructures can be envisioned to act as carriers of other biomaterials essential to investigating microstructure-function and nanostructure-function relationships in lipids and biology in general. This optical quality-control approach may be especially useful for determining the height of large-area features, where AFM scanning is not practical. For example, systems where this approach is promising include the analysis of ultrasmall liquid droplets, matrix-assisted dip-pen nanolithography, polymer-pen lithography, and especially the characterization of lipid structures.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as nonlimiting examples and are, therefore, not to be taken as limiting the various aspects so illustrated.

While the present invention has been disclosed with references to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A device comprising:
   a substrate, and
   a quorum sensor array on the substrate,
   wherein the quorum sensor array comprises quorum sensors that release signal molecules in response to one or more environmental signals being sensed by the quorum sensors to thereby amplify the one or more environmental signals by causing a signal chain reaction in neighboring quorum sensors of the quorum sensor array, and
   wherein each of the quorum sensors comprises a lipid multilayer structure.

2. The device of claim 1, wherein each of the quorum sensors comprises a lipid multilayer structure comprising a sensor mechanism for sensing the one or more environmental signals and a release mechanism for releasing one or more signal molecules in response to the sensor mechanism sensing the one or more environmental signals.

3. The device of claim 1, wherein each of the quorum sensors comprise one or more bacteria encapsulated within or bound to the lipid multilayer structure for sensing the one or more environmental signals and for releasing one or more signal molecules in response to one or more bacteria sensing the one or more environmental signals.

4. The device of claim 3, wherein at least some of the quorum sensors comprise bacteria encapsulated within a lipid multilayer structure.

5. The device of claim 3, wherein at least some of the quorum sensors comprise bacteria bound to a lipid multilayer structure.

6. The device of claim 3, wherein the one or more bacteria are the same species of bacteria for each of the quorum sensors.

7. The device of claim 3, wherein a first quorum sensor of the quorum sensor array comprises first species of and a second quorum sensor of the quorum sensor array comprises a second species of bacteria.

8. The device of claim 1, wherein the device comprises a detector for light scattered by at least a portion of the quorum sensor array.

9. The device of claim 8, wherein the device comprises a light source for exposing the quorum sensor array to light to thereby produce the light that is scattered by the quorum sensor array and detected by the detector.

10. The device of claim 1, wherein at least some lipid multilayer structures of the quorum sensor array comprise a mixture of two or more lipids.

11. A method comprising:
providing data for changes in optical properties of at least part of a quorum sensor array, on a substrate, in response to exposing the quorum sensor array to one or more environmental signals, and
determining the presence of the one or more environmental signals based on the data for changes in optical properties,
wherein the quorum sensor array comprises quorum sensors that release signal molecules in response to the one or more environmental signals interacting the quorum sensors to thereby amplify the one or more environmental signals by causing a signal chain reaction in neighboring quorum sensors of the quorum sensor array, and
wherein each of the quorum sensors comprises a lipid multilayer structure.

12. The method of claim 11, wherein the data is for changes in light scattered by one or more portions of the quorum sensor array.

13. The method of claim 11, wherein the method comprises:
detecting changes in optical properties of at least part of the quorum sensor array in response to exposing the quorum sensor array to the one or more environmental signals, and
generating the data for the changes in optical properties based on the detected changes in optical properties.

14. The method of claim 13, wherein detecting the changes in optical properties comprises detecting light scattered by at least part of the quorum sensor array.

15. The method of claim 11, wherein each of the quorum sensors comprises a lipid multilayer structure comprising a sensor mechanism for sensing the one or more environmental signals and a release mechanism for releasing one or more signal molecules in response to the sensor mechanism sensing the one or more environmental signals.

16. The method of claim 11, wherein each of the quorum sensors comprise one or more bacteria encapsulated within or bound to the lipid multilayer structure for sensing the one or more environmental signals and for releasing one or more signal molecules in response to one or more bacteria sensing the one or more environmental signals.

17. The method of claim 16, wherein at least some of the quorum sensors comprise bacteria encapsulated within a lipid multilayer structure.

18. The method of claim 16, wherein at least some of the quorum sensors comprise bacteria bound to a lipid multilayer structure.

19. The method of claim 16, wherein the one or more bacteria are the same species of bacteria for each of the quorum sensors.

20. The method of claim 16, wherein a first quorum sensor of the quorum sensor array comprises first species of and a second quorum sensor of the quorum sensor array comprises a second species of bacteria.

21. The method of claim 11, wherein at least some lipid multilayer structures of the quorum sensor array comprise a mixture of two or more lipids.

22. The device of claim 1, wherein the lipid multilayer structure is located on the substrate.

23. The device of claim 22, wherein the quorum sensor array comprises an array of lipid multilayer structures on the substrate, and wherein the lipid multilayer structure of each quorum sensor is one of the lipid multilayer structures of the array of lipid multilayer structures.

24. The method of claim 11, wherein the lipid multilayer structure is located on the substrate.

25. The method of claim 24, wherein the quorum sensor array comprises an array of lipid multilayer structures on the substrate, and wherein the lipid multilayer structure of each quorum sensor is one of the lipid multilayer structures of the array of lipid multilayer structures.

* * * * *